(12) United States Patent
Komori et al.

(10) Patent No.: US 7,956,010 B2
(45) Date of Patent: *Jun. 7, 2011

(54) AMIDE COMPOUND AND USE THEREOF FOR CONTROLLING PLANT DISEASES

(75) Inventors: Takashi Komori, Tokyo (JP); Mayumi Kubota, Toyonaka (JP); Yuichi Matsuzaki, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/451,126

(22) PCT Filed: Apr. 25, 2008

(86) PCT No.: PCT/JP2008/058032
§ 371 (c)(1),
(2), (4) Date: Oct. 27, 2009

(87) PCT Pub. No.: WO2008/136388
PCT Pub. Date: Nov. 13, 2008

(65) Prior Publication Data
US 2010/0048701 A1    Feb. 25, 2010

(30) Foreign Application Priority Data
Apr. 27, 2007    (JP) ................. 2007-118647

(51) Int. Cl.
*A01N 37/18* (2006.01)
*C07C 233/00* (2006.01)
(52) U.S. Cl. ................. 504/337; 564/183
(58) Field of Classification Search ........ 562/512, 562/588; 564/171, 184, 183; 504/337
See application file for complete search history.

(56) References Cited

U.S. PATENT DOCUMENTS

| | | | |
|---|---|---|---|
| 4,946,865 | A | 8/1990 | Takahashi et al. |
| 2004/0049065 | A1 | 3/2004 | Craig et al. |
| 2004/0248739 | A1 | 12/2004 | Schaetzer et al. |
| 2008/0319080 | A1 | 12/2008 | Komori |
| 2009/0131531 | A1 | 5/2009 | Komori |
| 2010/0105647 | A1* | 4/2010 | Komori et al. ........... 514/183 |

FOREIGN PATENT DOCUMENTS

| | | |
|---|---|---|
| EP | 1295868 * | 3/2003 |
| EP | 1 770 085 A1 | 4/2007 |
| JP | 63-154601 | 6/1988 |
| JP | 2004-74537 | 3/2004 |
| WO | 03/104206 | 12/2003 |
| WO | 2004/002981 | 1/2004 |
| WO | 2007/049728 | 5/2007 |
| WO | 2007/049729 | 5/2007 |
| WO | 2008/136385 | 11/2008 |
| WO | 2008/136387 | 11/2008 |
| WO | 2008/136389 | 11/2008 |
| WO | 2009/004978 | 1/2009 |
| WO | 2009/011305 | 1/2009 |

OTHER PUBLICATIONS

Patani et al., Chem. Rev., 1996, 96, p. 3149.*
Supplementary European Search Report issued Mar. 24, 2010 in European Application No. 08752106.8.
Linda J. Ejim et al., "Inhibitors of Bacterial Cystathionine β-Lyase: Leads for New Antimicrobial Agents and Probes of Enzyme Structure and Function," J. Med. Chem., 50(4), 755-764 (2007).
Jun-Ying Nie et al., "Synthesis of fluoro- and polyfluoro-veratraldehydes by electrophilic fluorination", Journal of Fluorine Chemistry, 74(2), 297-301 (1995).
International Search Report issued Jul. 15, 2008 in International (PCT) Application No. PCT/JP2008/058032.
Abstract of JP 2007-145816, published Jun. 14, 2007.
Abstract of JP 2007-145817, published Jun. 14, 2007.
Abstract of JP 63-027450, published Feb. 5, 1988.

* cited by examiner

*Primary Examiner* — Rebecca L Anderson
*Assistant Examiner* — Samantha L Shterengarts
(74) *Attorney, Agent, or Firm* — Wenderoth, Lind & Ponack, L.L.P.

(57) ABSTRACT

Disclosed is an amide compound represented by the formula (1) below, which has excellent plant disease controlling activity.

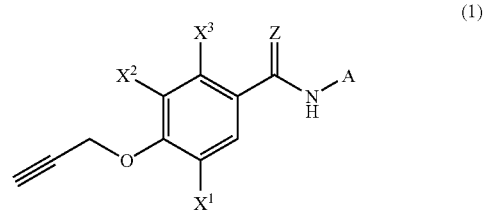

(1)

In the formula, $X^1$ represents a fluorine atom or a methoxy group; $X^2$ represents a hydrogen atom, a halogen atom, a $C_1$-$C_4$ alkyl group or the like; $X^3$ represents a halogen atom, a $C_1$-$C_4$ alkyl group or the like; Z represents an oxygen atom or a sulfur atom; and A represents an $A^1$-$CR^{11}R^{12}R^{13}$ group, an $A^2$-$Cy^1$ group or an $A^3$-$Cy^2$ group, wherein $A^1$ represents a $CH_2$ group or the like, $A^2$ represents a single bond, a $CH_2$ group or the like, $A^3$ represents a $C_1$-$C_3$ haloalkyl group, a $C_2$-$C_4$ alkenyl group or the like, $Cy^1$ represents a $C_3$-$C_6$ cycloalkyl group substituted with a $C_1$-$C_6$ alkoxy group or the like, $Cy^2$ represents a $C_3$-$C_6$ cycloalkyl group which may be substituted with a halogen atom or the like, $R^{11}$ and $R^{12}$ independently represent a $C_1$-$C_4$ alkyl group, and $R^{13}$ represents a halogen atom, a hydroxyl group or the like.

10 Claims, No Drawings

AMIDE COMPOUND AND USE THEREOF FOR CONTROLLING PLANT DISEASES

TECHNICAL FIELD

The present invention relates to an amide compound and use thereof for controlling plant diseases.

BACKGROUND ART

Drugs for controlling plant diseases have been conventionally developed. Compounds having plant disease controlling activity have been found out and have been put into practice.

DISCLOSURE OF THE INVENTION

Problems to be Solved by the Invention

An object of the present invention is to provide a compound having excellent plant disease controlling activity.

Means for Solving the Problems

The present inventors intensively studied in order to find out a compound having excellent plant disease controlling efficacy and, as a result, found that an amide compound represented by the following formula (1) has excellent plant disease controlling activity. Thus the present invention was completed.

The present invention provides an amide compound represented by the formula (1):

[Chemical formula 1]

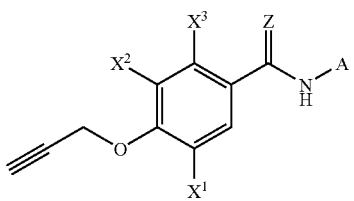

(1)

which is hereinafter, referred to as the compound of the present invention,
wherein $X^1$ represents a fluorine atom or a methoxy group, $X^2$ represents a hydrogen atom, a halogen atom, a $C_1$-$C_4$ alkyl group, a $C_2$-$C_4$ alkenyl group, a $C_2$-$C_4$ alkynyl group, a $C_1$-$C_4$ haloalkyl group, a $C_1$-$C_4$ alkoxy group, a $C_1$-$C_4$ alkylthio group, a hydroxy $C_1$-$C_4$ alkyl group, a nitro group, a cyano group, a formyl group, an $NR^1R^2$ group, a $CO_2R^3$ group, a $CONR^4R^5$ group, or a phenyl group optionally substituted with at least one group selected from the group consisting of a methyl group, a halogen atom, a cyano group and a nitro group, $X^3$ represents a halogen atom, a $C_1$-$C_4$ alkyl group, a $C_2$-$C_4$ alkenyl group, a $C_2$-$C_4$ alkynyl group, a $C_1$-$C_4$ haloalkyl group, a $C_1$-$C_4$ alkoxy group, a $C_1$-$C_4$ alkylthio group, a nitro group, a cyano group, a formyl group, an $NR^6R^7$ group, a $CO_2R^8$ group, a $CONR^9R^{10}$ group, or a phenyl group optionally substituted with at least one group selected from the group consisting of a methyl group, a halogen atom, a cyano group and a nitro group, Z represents an oxygen atom or a sulfur atom, A represents a group represented by $A^1$-$CR^{11}R^{12}R^{13}$, $A^2$-$Cy^1$ or $A^3$-$Cy^2$, $A^1$ represents a $CH_2$ group, a $CH(CH_3)$ group, a $C(CH_3)_2$ group or a $CH(CH_2CH_3)$ group, $A^2$ represents a single bond, a $CH_2$ group, a $CH(CH_3)$ group, a $C(CH_3)_2$ group or a $CH(CH_2CH_3)$ group, $A^3$ represents a methylene group substituted with at least one group selected from the group consisting of a $C_1$-$C_3$ haloalkyl group, a $C_2$-$C_4$ alkenyl group, a $C_2$-$C_4$ alkynyl group, a cyano group, a phenyl group and a $C_2$-$C_5$ alkoxycarbonyl group, $Cy^1$ represents a $C_3$-$C_6$ cycloalkyl group substituted with at least one group selected from the following group [a-1], a $C_3$-$C_6$ cycloalkenyl group optionally substituted with at least one group selected from the following group [a-1], a $C_3$-$C_6$ cycloalkyl group which is optionally substituted with at least one group selected from the following group [a-1] and in which one of methylenes forming the ring is replaced with a carbonyl group, or a $C_3$-$C_6$ hydroxyiminocycloalkyl group optionally substituted with at least one group selected from the following group [a-1], $Cy^2$ represents a $C_3$-$C_6$ cycloalkyl group optionally substituted with at least one group selected from the following group [a-2], a $C_3$-$C_6$ cycloalkenyl group optionally substituted with at least one group selected from the following group [a-2], a $C_3$-$C_6$ cycloalkyl group which is optionally substituted with at least one group selected from the following group [a-2] and in which one of methylenes forming the ring is replaced with a carbonyl group, or a $C_3$-$C_6$ hydroxyiminocycloalkyl group optionally substituted with at least one group selected from the following group [a-2], $R^1$ and $R^2$ independently represent a hydrogen atom, a $C_1$-$C_4$ alkyl group, a $C_3$-$C_4$ alkenyl group, a $C_3$-$C_4$ alkynyl group, a $C_2$-$C_4$ haloalkyl group, a $C_2$-$C_5$ alkylcarbonyl group, a $C_2$-$C_5$ alkoxycarbonyl group or a $C_1$-$C_4$ alkylsulfonyl group, $R^3$ represents a $C_1$-$C_4$ alkyl group, a $C_3$-$C_4$ alkenyl group or a $C_3$-$C_4$ alkynyl group, $R^4$ represents a hydrogen atom, a $C_1$-$C_4$ alkyl group, a $C_3$-$C_4$ alkenyl group, a $C_3$-$C_4$ alkynyl group, a $C_2$-$C_4$ haloalkyl group, a $C_2$-$C_5$ alkylcarbonyl group, a $C_2$-$C_5$ alkoxycarbonyl group or a $C_1$-$C_4$ alkylsulfonyl group, $R^5$ represents a hydrogen atom, a $C_1$-$C_4$ alkyl group, a $C_3$-$C_4$ alkenyl group, a $C_3$-$C_4$ alkynyl group, or a $C_2$-$C_4$ haloalkyl group, $R^6$ and $R^7$ independently represent a hydrogen atom, a $C_1$-$C_4$ alkyl group, a $C_3$-$C_4$ alkenyl group, a $C_3$-$C_4$ alkynyl group, a $C_2$-$C_4$ haloalkyl group, a $C_2$-$C_5$ alkylcarbonyl group, a $C_2$-$C_5$ alkoxycarbonyl group or a $C_1$-$C_4$ alkylsulfonyl group, $R^8$ represents a $C_1$-$C_4$ alkyl group, a $C_3$-$C_4$ alkenyl group or a $C_3$-$C_4$ alkynyl group, $R^9$ represents a hydrogen atom, a $C_1$-$C_4$ alkyl group, a $C_3$-$C_4$ alkenyl group, a $C_3$-$C_4$ alkynyl group, a $C_2$-$C_4$ haloalkyl group, a $C_2$-$C_5$ alkylcarbonyl group, a $C_2$-$C_5$ alkoxycarbonyl group or a $C_1$-$C_4$ alkylsulfonyl group, $R^{10}$ represents a hydrogen atom, a $C_1$-$C_4$ alkyl group, a $C_3$-$C_4$ alkenyl group, a $C_3$-$C_4$ alkynyl group, or a $C_2$-$C_4$ haloalkyl group, $R^{11}$ and $R^{12}$ independently represent a $C_1$-$C_4$ alkyl group, $R^{13}$ represents a halogen atom, a hydroxyl group, a $C_1$-$C_6$ alkyl group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a hydroxy $C_1$-$C_6$ alkyl group, a $C_2$-$C_4$ alkylcarbonyloxy group, a $(C_1$-$C_3$ alkylamino)$C_1$-$C_6$ alkyl group, a $(di(C_1$-$C_3)$alkyl)amino)$C_1$-$C_6$ alkyl group, a mercapto group, a carbamoyl group, a formyl group, a $C_2$-$C_6$ cyanoalkyl group, a $C_1$-$C_3$ alkylsulfonyl group, a phenoxy group or an $NR^{14}R^{15}$ group [wherein $R^{14}$ and $R^{15}$ independently represent a hydrogen atom, a $C_1$-$C_4$ alkyl group, a $C_2$-$C_5$ alkylcarbonyl group, a $C_2$-$C_5$ alkoxycarbonyl group, or a $C_1$-$C_4$ alkylsulfonyl group];

the group [a-1] consists of:
a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a $C_1$-$C_3$ alkylidene group which forms a double bond with the same carbon atom forming a ring, a hydroxy $C_1$-$C_6$ alkyl group, a $C_2$-$C_4$ alkylcarbonyloxy group, a ($C_1$-$C_3$ alkylamino)$C_1$-$C_6$ alkyl group, a (di($C_1$-$C_3$ alkyl)amino)$C_1$-$C_6$ alkyl group, a mercapto group, a carbamoyl group, a formyl group, a $C_2$-$C_6$ cyanoalkyl group, a $C_1$-$C_3$ alkylsulfonyl group, a phenoxy group, and an $NR^{16}R^{17}$ group [wherein $R^{16}$ and $R^{17}$ independently represent a hydrogen atom, a $C_1$-$C_4$ alkyl group, a $C_2$-$C_5$ alkylcarbonyl group, a $C_2$-$C_5$ alkoxycarbonyl group or a $C_1$-$C_4$ alkylsulfonyl group]; and the group [a-2] consists of:
a halogen atom, a $C_1$-$C_4$ alkyl group, a $C_2$-$C_4$ alkenyl group, a $C_2$-$C_4$ alkynyl group, a hydroxyl group, a cyano group, a carboxyl group, a $C_2$-$C_5$ alkoxycarbonyl group, a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a $C_1$-$C_3$ alkylidene group which forms a double bond with the same carbon atom forming a ring, a hydroxy $C_1$-$C_6$ alkyl group, a $C_2$-$C_4$ alkylcarbonyloxy group, a ($C_1$-$C_3$ alkylamino)$C_1$-$C_6$ alkyl group, a (di($C_1$-$C_3$ alkyl)amino)$C_1$-$C_6$ alkyl group, a mercapto group, a carbamoyl group, a formyl group, a $C_2$-$C_6$ cyanoalkyl group, a $C_1$-$C_3$ alkylsulfonyl group, a phenoxy group, and an $NR^{18}R^{19}$ group [wherein $R^{18}$ and $R^{19}$ independently represent a hydrogen atom, a $C_1$-$C_4$ alkyl group, a $C_2$-$C_5$ alkylcarbonyl group, a $C_2$-$C_5$ alkoxycarbonyl group or a $C_1$-$C_4$ alkylsulfonyl group], a plant disease controlling composition containing the compound of the present invention as an active ingredient, and a plant disease controlling method which comprises treating a plant or soil with an effective amount of the compound of the present invention.

EFFECTS OF THE INVENTION

The compound of the present invention has excellent plant disease controlling activity and therefore, it is useful as an active ingredient of a plant disease controlling composition.

BEST MODE FOR CARRYING OUT THE INVENTION

In the present invention, examples of the halogen atom represented by $X^2$ include a fluorine atom, a chlorine atom, a bromine atom and an iodine atom.

Examples of the $C_1$-$C_4$ alkyl group represented by $X^2$ include a methyl group, an ethyl group, a 1-methylethyl group, a 1,1-dimethylethyl group, a propyl group, and a 1-methylpropyl group.

Examples of the $C_2$-$C_4$ alkenyl group represented by $X^2$ include a vinyl group, a 1-propenyl group, a 2-propenyl group, a 2-butenyl group and a 3-butenyl group.

Examples of the $C_2$-$C_4$ alkynyl group represented by $X^2$ include an ethynyl group, a 1-propynyl group, a 2-propynyl group, and a 3-butynyl group.

Examples of the $C_1$-$C_4$ haloalkyl group represented by $X^2$ include a fluoromethyl group, a chloromethyl group, a bromomethyl group, a difluoromethyl group, a dichloromethyl group, a dibromomethyl group, a trifluoromethyl group, a trichloromethyl group, a dichlorofluoromethyl group, a chlorodifluoromethyl group, a 1,1-difluoroethyl group, a 2,2,2-trifluoroethyl group, a 2-fluoroethyl group, a 3-fluoropropyl group, a 4-fluorobutyl group and a 1-chloroethyl group.

Examples of the $C_1$-$C_4$ alkoxy group represented by $X^2$ include a methoxy group, an ethoxy group, a 1-methylethoxy group, a 1,1-dimethylethoxy group, a propoxy group, a 1-methylpropoxy group, a 2-methylpropoxy group and a butoxy group.

Examples of the $C_1$-$C_4$ alkylthio group represented by $X^2$ include a methylthio group, an ethylthio group, a 1-methylethylthio group, a 1,1-dimethylethylthio group, a propylthio group and a 1-methylpropylthio group.

Examples of the hydroxy $C_1$-$C_4$ alkyl group represented by $X^2$ include a hydroxymethyl group, a 1-hydroxyethyl group and a 2-hydroxyethyl group.

Examples of the phenyl group optionally substituted with at least one group selected from the group consisting of a methyl group, a halogen atom, a cyano group and a nitro group which is represented by $X^2$ include a phenyl group, a 2-methylphenyl group, a 3-methylphenyl group, a 4-methylphenyl group, a 2-fluorophenyl group, a 3-fluorophenyl group, a 4-fluorophenyl group, a 2-chlorophenyl group, a 3-chlorophenyl group, a 4-chlorophenyl group, a 4-cyanophenyl group and a 4-nitrophenyl group.

Examples of the halogen atom represented by $X^3$ include a fluorine atom, a chlorine atom, a bromine atom and an iodine atom.

Examples of the $C_1$-$C_4$ alkyl group represented by $X^3$ include a methyl group, an ethyl group, a 1-methylethyl group, a 1,1-dimethylethyl group, a propyl group, and a 1-methylpropyl group.

Examples of the $C_2$-$C_4$ alkenyl group represented by $X^3$ include a vinyl group, a 1-propenyl group, a 2-propenyl group, a 2-butenyl group and a 3-butenyl group.

Examples of the $C_2$-$C_4$ alkynyl group represented by $X^3$ include an ethynyl group, a 1-propynyl group, a 2-propynyl group, and a 3-butynyl group.

Examples of the $C_1$-$C_4$ haloalkyl group represented by $X^3$ include a fluoromethyl group, a chloromethyl group, a bromomethyl group, a difluoromethyl group, a dichloromethyl group, a dibromomethyl group, a trifluoromethyl group, a trichloromethyl group, a dichlorofluoromethyl group, a chlorodifluoromethyl group, a 1,1-difluoroethyl group, a 2,2,2-trifluoroethyl group, a 2-fluoroethyl group, a 3-fluoropropyl group, a 4-fluorobutyl group and a 1-chloroethyl group.

Examples of the $C_1$-$C_4$ alkoxy group represented by $X^3$ include a methoxy group, an ethoxy group, a 1-methylethoxy group, a 1,1-dimethylethoxy group, a propoxy group, a 1-methylpropoxy group, a 2-methylpropoxy group and a butoxy group.

Examples of the $C_1$-$C_4$ alkylthio group represented by $X^3$ include a methylthio group, an ethylthio group, a 1-methylethylthio group, a 1,1-dimethylethylthio group, a propylthio group and a 1-methylpropylthio group.

Examples of the phenyl group optionally substituted with at least one group selected from the group consisting of a methyl group, a halogen atom, a cyano group and a nitro group which is represented by $X^3$ include a phenyl group, a 2-methylphenyl group, a 3-methylphenyl group, a 4-methylphenyl group, a 2-fluorophenyl group, a 3-fluorophenyl group, a 4-fluorophenyl group, a 2-chlorophenyl group, a 3-chlorophenyl group, a 4-chlorophenyl group, a 4-cyanophenyl group and a 4-nitrophenyl group.

Examples of the $C_1$-$C_3$ haloalkyl group in the methylene group substituted with at least one group selected from the group consisting of a $C_1$-$C_3$ haloalkyl group, a $C_2$-$C_4$ alkenyl group, a $C_2$-$C_4$ alkynyl group, a cyano group, a phenyl group and a $C_2$-$C_5$ alkoxycarbonyl group which is represented by $A^3$ include a fluoromethyl group, a chloromethyl group, a bromomethyl group, a difluoromethyl group, a dichloromethyl group, a dibromomethyl group, a trifluoromethyl group, a trichloromethyl group, a dichlorofluoromethyl group, a chlorodifluoromethyl group, a 1,1-difluoroethyl group, a 2,2,2-trifluoroethyl group, a 2-fluoroethyl group, a 3-fluoropropyl group, and a 1-chloroethyl group.

Examples of the $C_2$-$C_4$ alkenyl group in the methylene group substituted with at least one group selected from the group consisting of a $C_1$-$C_3$ haloalkyl group, a $C_2$-$C_4$ alkenyl group, a $C_2$-$C_4$ alkynyl group, a cyano group, a phenyl group and a $C_2$-$C_5$ alkoxycarbonyl group which is represented by $A^3$ include a vinyl group, a 1-propenyl group, a 2-propenyl group, a 2-butenyl group and a 3-butenyl group.

Examples of the $C_2$-$C_4$ alkynyl group in the methylene group substituted with at least one group selected from the group consisting of a $C_1$-$C_3$ haloalkyl group, a $C_2$-$C_4$ alkenyl group, a $C_2$-$C_4$ alkynyl group, a cyano group, a phenyl group and a $C_2$-$C_5$ alkoxycarbonyl group which is represented by $A^3$ include an ethynyl group, a 1-propynyl group, a 2-propynyl group, and a 3-butynyl group.

Examples of the $C_2$-$C_5$ alkoxycarbonyl group in the methylene group substituted with at least one group selected from the group consisting of a $C_1$-$C_3$ haloalkyl group, a $C_2$-$C_4$ alkenyl group, a $C_2$-$C_4$ alkynyl group, a cyano group, a phenyl group and a $C_2$-$C_5$ alkoxycarbonyl group which is represented by $A^3$ include a methoxycarbonyl group, an ethoxycarbonyl group, a 1-methylethoxycarbonyl group, and a 1,1-dimethylethoxycarbonyl group.

Examples of the methylene group substituted with at least one group selected from the group consisting of a $C_1$-$C_3$ haloalkyl group, a $C_2$-$C_4$ alkenyl group, a $C_2$-$C_4$ alkynyl group, a cyano group, a phenyl group and a $C_2$-$C_5$ alkoxycarbonyl group which is represented by $A^3$ include specifically $CH(CF_3)$, $CH(CF_2H)$, $CH(CFH_2)$, $CH(CH_2CF_3)$, $CH(CCl_3)$, $CH(CCl_2H)$, $CH(CClH_2)$, $CH(CH=CH_2)$, $CH(CH=CHCH_3)$, $CH(CH=C(CH_3)_2)$, $CH(C\equiv CH)$, $CH(C\equiv CCH_3)$, $CH(CH_2C\equiv CH)$, $CH(CN)$, $CH(C_6H_5)$, $CH(CO_2CH_3)$, $CH(CO_2CH_2CH_3)$, and $CH(CO_2CH(CH_3)_2)$ Examples of the $C_1$-$C_4$ alkyl group represented by $R^1$ include a methyl group, an ethyl group, a 1-methylethyl group, a 1,1-dimethylethyl group, a propyl group and a 1-methylpropyl group.

Examples of the $C_3$-$C_4$ alkenyl group represented by $R^1$ include a 1-propenyl group, a 2-propenyl group, a 2-butenyl group and a 3-butenyl group.

Examples of the $C_3$-$C_4$ alkynyl group represented by $R^1$ include a 1-propynyl group, a 2-propynyl group and a 3-butynyl group.

Examples of the $C_2$-$C_4$ haloalkyl group represented by $R^1$ include a 1,1-difluoroethyl group, a 2,2,2-trifluoroethyl group, a 2-fluoroethyl group, a 3-fluoropropyl group, a 4-fluorobutyl group and a 1-chloroethyl group.

Examples of the $C_2$-$C_5$ alkylcarbonyl group represented by $R^1$ include an acetyl group, an ethylcarbonyl group, a 1-methylethylcarbonyl group and a 1,1-dimethylethylcarbonyl group.

Examples of the $C_2$-$C_5$ alkoxycarbonyl group represented by $R^1$ include a methoxycarbonyl group, an ethoxycarbonyl group, a 1-methylethoxycarbonyl group and a 1,1-dimethylethoxycarbonyl group.

Examples of the $C_1$-$C_4$ alkylsulfonyl group represented by $R^1$ include a methylsulfonyl group, an ethylsulfonyl group, a 1-methylethylsulfonyl group and a 1,1-dimethylethylsulfonyl group.

Examples of the $C_1$-$C_4$ alkyl group represented by $R^2$ include a methyl group, an ethyl group, a 1-methylethyl group, a 1,1-dimethylethyl group, a propyl group and a 1-methylpropyl group.

Examples of the $C_3$-$C_4$ alkenyl group represented by $R^2$ include a 1-propenyl group, a 2-propenyl group, a 2-butenyl group and a 3-butenyl group.

Examples of the $C_3$-$C_4$ alkynyl group represented by $R^2$ include a 1-propynyl group, a 2-propynyl group and a 3-butynyl group.

Examples of the $C_2$-$C_4$ haloalkyl group represented by $R^2$ include a 1,1-difluoroethyl group, a 2,2,2-trifluoroethyl group, a 2-fluoroethyl group, a 3-fluoropropyl group, a 4-fluorobutyl group and a 1-chloroethyl group.

Examples of the $C_2$-$C_5$ alkylcarbonyl group represented by $R^2$ include an acetyl group, an ethylcarbonyl group, a 1-methylethylcarbonyl group and a 1,1-dimethylethylcarbonyl group.

Examples of the $C_2$-$C_5$ alkoxycarbonyl group represented by $R^2$ include a methoxycarbonyl group, an ethoxycarbonyl group, a 1-methylethoxycarbonyl group and a 1,1-dimethylethoxycarbonyl group.

Examples of the $C_1$-$C_4$ alkylsulfonyl group represented by $R^2$ include a methylsulfonyl group, an ethylsulfonyl group, a 1-methylethylsulfonyl group and a 1,1-dimethylethylsulfonyl group.

Examples of the $C_1$-$C_4$ alkyl group represented by $R^3$ include a methyl group, an ethyl group, a 1-methylethyl group, a 1,1-dimethylethyl group, a propyl group and a 1-methylpropyl group.

Examples of the $C_3$-$C_4$ alkenyl group represented by $R^3$ include a 1-propenyl group, a 2-propenyl group, a 2-butenyl group and a 3-butenyl group.

Examples of the $C_3$-$C_4$ alkynyl group represented by $R^3$ include a 1-propynyl group, a 2-propynyl group and a 3-butynyl group.

Examples of the $C_1$-$C_4$ alkyl group represented by $R^4$ include a methyl group, an ethyl group, a 1-methylethyl group, a 1,1-dimethylethyl group, a propyl group and a 1-methylpropyl group.

Examples of the $C_3$-$C_4$ alkenyl group represented by $R^4$ include a 1-propenyl group, a 2-propenyl group, a 2-butenyl group and a 3-butenyl group.

Examples of the $C_3$-$C_4$ alkynyl group represented by $R^4$ include a 1-propynyl group, a 2-propynyl group and a 3-butynyl group.

Examples of the $C_2$-$C_4$ haloalkyl group represented by $R^4$ include a 1,1-difluoroethyl group, a 2,2,2-trifluoroethyl group, a 2-fluoroethyl group, a 3-fluoropropyl group, a 4-fluorobutyl group and a 1-chloroethyl group.

Examples of the $C_2$-$C_5$ alkylcarbonyl group represented by $R^4$ include an acetyl group, an ethylcarbonyl group, a 1-methylethylcarbonyl group and a 1,1-dimethylethylcarbonyl group.

Examples of the $C_2$-$C_5$ alkoxycarbonyl group represented by $R^4$ include a methoxycarbonyl group, an ethoxycarbonyl group, a 1-methylethoxycarbonyl group and a 1,1-dimethylethoxycarbonyl group.

Examples of the $C_1$-$C_4$ alkylsulfonyl group represented by $R^4$ include a methylsulfonyl group, an ethylsulfonyl group, a 1-methylethylsulfonyl group and a 1,1-dimethylethylsulfonyl group.

Examples of the $C_1$-$C_4$ alkyl group represented by $R^5$ include a methyl group, an ethyl group, a 1-methylethyl group, a 1,1-dimethylethyl group, a propyl group and a 1-methylpropyl group.

Examples of the $C_3$-$C_4$ alkenyl group represented by $R^5$ include a 1-propenyl group, a 2-propenyl group, a 2-butenyl group and a 3-butenyl group.

Examples of the $C_3$-$C_4$ alkynyl group represented by $R^5$ include a 1-propynyl group, a 2-propynyl group and a 3-butynyl group.

Examples of the $C_2$-$C_4$ haloalkyl group represented by $R^5$ include a 1,1-difluoroethyl group, a 2,2,2-trifluoroethyl group, a 2-fluoroethyl group, a 3-fluoropropyl group, a 4-fluorobutyl group and a 1-chloroethyl group.

Examples of the $NR^1R^2$ group include an amino group, a methylamino group, a dimethylamino group, an ethylamino group, a 2-propenylamino group, a 2-propynylamino group, a 2-chloroethylamino group, an acetylamino group, a propionylamino group, a 1,1-dimethylethylcarbonylamino group, a methoxycarbonylamino group, an ethoxycarbonylamino group, a methanesulfonylamino group, an N-acetyl-N-methylamino group, an N-ethoxycarbonyl-N-methylamino group and a methanesulfonylmethylamino group.

Examples of the $CONR^4R^5$ group include a carbamoyl group, a methylcarbamoyl group, a dimethylcarbamoyl group, an ethylmethylcarbamoyl group, a (2-propenyl)carbamoyl group, a (2-propynyl)carbamoyl group and a 2-chloroethylcarbamoyl group.

Examples of the $C_1$-$C_4$ alkyl group represented by $R^6$ include a methyl group, an ethyl group, a 1-methylethyl group, a 1,1-dimethylethyl group, a propyl group and a 1-methylpropyl group.

Examples of the $C_3$-$C_4$ alkenyl group represented by $R^6$ include a 1-propenyl group, a 2-propenyl group, a 2-butenyl group and a 3-butenyl group.

Examples of the $C_3$-$C_4$ alkynyl group represented by $R^6$ include a 1-propynyl group, a 2-propynyl group and a 3-butynyl group.

Examples of the $C_2$-$C_4$ haloalkyl group represented by $R^6$ include a 1,1-difluoroethyl group, a 2,2,2-trifluoroethyl group, a 2-fluoroethyl group, a 3-fluoropropyl group, a 4-fluorobutyl group and a 1-chloroethyl group.

Examples of the $C_2$-$C_5$ alkylcarbonyl group represented by $R^6$ include an acetyl group, an ethylcarbonyl group, a 1-methylethylcarbonyl group and a 1,1-dimethylethylcarbonyl group.

Examples of the $C_2$-$C_5$ alkoxycarbonyl group represented by $R^6$ include a methoxycarbonyl group, an ethoxycarbonyl group, a 1-methylethoxycarbonyl group and a 1,1-dimethylethoxycarbonyl group.

Examples of the $C_1$-$C_4$ alkylsulfonyl group represented by $R^6$ include a methylsulfonyl group, an ethylsulfonyl group, a 1-methylethylsulfonyl group and a 1,1-dimethylethylsulfonyl group.

Examples of the $C_1$-$C_4$ alkyl group represented by $R^7$ include a methyl group, an ethyl group, a 1-methylethyl group, a 1,1-dimethylethyl group, a propyl group and a 1-methylpropyl group.

Examples of the $C_3$-$C_4$ alkenyl group represented by $R^7$ include a 1-propenyl group, a 2-propenyl group, a 2-butenyl group and a 3-butenyl group.

Examples of the $C_3$-$C_4$ alkynyl group represented by $R^7$ include a 1-propynyl group, a 2-propynyl group and a 3-butynyl group.

Examples of the $C_2$-$C_4$ haloalkyl group represented by $R^7$ include a 1,1-difluoroethyl group, a 2,2,2-trifluoroethyl group, a 2-fluoroethyl group, a 3-fluoropropyl group, a 4-fluorobutyl group and a 1-chloroethyl group.

Examples of the $C_2$-$C_5$ alkylcarbonyl group represented by $R^7$ include an acetyl group, an ethylcarbonyl group, a 1-methylethylcarbonyl group and a 1,1-dimethylethylcarbonyl group.

Examples of the $C_2$-$C_5$ alkoxycarbonyl group represented by $R^7$ include a methoxycarbonyl group, an ethoxycarbonyl group, a 1-methylethoxycarbonyl group and a 1,1-dimethylethoxycarbonyl group.

Examples of the $C_1$-$C_4$ alkylsulfonyl group represented by $R^7$ include a methylsulfonyl group, an ethylsulfonyl group, a 1-methylethylsulfonyl group and a 1,1-dimethylethylsulfonyl group.

Examples of the $C_1$-$C_4$ alkyl group represented by $R^8$ include a methyl group, an ethyl group, a 1-methylethyl group, a 1,1-dimethylethyl group, a propyl group and a 1-methylpropyl group.

Examples of the $C_3$-$C_4$ alkenyl group represented by $R^8$ include a 1-propenyl group, a 2-propenyl group, a 2-butenyl group and a 3-butenyl group.

Examples of the $C_3$-$C_4$ alkynyl group represented by $R^8$ include a 1-propynyl group, a 2-propynyl group and a 3-butynyl group.

Examples of the $C_1$-$C_4$ alkyl group represented by $R^9$ include a methyl group, an ethyl group, a 1-methylethyl group, a 1,1-dimethylethyl group, a propyl group and a 1-methylpropyl group.

Examples of the $C_3$-$C_4$ alkenyl group represented by $R^9$ include a 1-propenyl group, a 2-propenyl group, a 2-butenyl group and a 3-butenyl group.

Examples of the $C_3$-$C_4$ alkynyl group represented by $R^9$ include a 1-propynyl group, a 2-propynyl group and a 3-butynyl group.

Examples of the $C_2$-$C_4$ haloalkyl group represented by $R^9$ include a 1,1-difluoroethyl group, a 2,2,2-trifluoroethyl group, a 2-fluoroethyl group, a 3-fluoropropyl group, a 4-fluorobutyl group and a 1-chloroethyl group.

Examples of the $C_2$-$C_5$ alkylcarbonyl group represented by $R^9$ include an acetyl group, an ethylcarbonyl group, a 1-methylethylcarbonyl group and a 1,1-dimethylethylcarbonyl group.

Examples of the $C_2$-$C_5$ alkoxycarbonyl group represented by $R^9$ include a methoxycarbonyl group, an ethoxycarbonyl group, a 1-methylethoxycarbonyl group and a 1,1-dimethylethoxycarbonyl group.

Examples of the $C_1$-$C_4$ alkylsulfonyl group represented by $R^9$ include a methylsulfonyl group, an ethylsulfonyl group, a 1-methylethylsulfonyl group and a 1,1-dimethylethylsulfonyl group.

Examples of the $C_1$-$C_4$ alkyl group represented by $R^{10}$ include a methyl group, an ethyl group, a 1-methylethyl group, a 1,1-dimethylethyl group, a propyl group and a 1-methylpropyl group.

Examples of the $C_3$-$C_4$ alkenyl group represented by $R^{10}$ include a 1-propenyl group, a 2-propenyl group, a 2-butenyl group and a 3-butenyl group.

Examples of the $C_3$-$C_4$ alkynyl group represented by $R^{10}$ include a 1-propynyl group, a 2-propynyl group and a 3-butynyl group.

Examples of the $C_2$-$C_4$ haloalkyl group represented by $R^{10}$ include a 1,1-difluoroethyl group, a 2,2,2-trifluoroethyl group, a 2-fluoroethyl group, a 3-fluoropropyl group, a 4-fluorobutyl group and a 1-chloroethyl group.

Examples of the $NR^6R^7$ group include an amino group, a methylamino group, a dimethylamino group, an ethylamino group, a 2-propenylamino group, a 2-propynylamino group, a 2-chloroethylamino group, an acetylamino group, a propionylamino group, a 1,1-dimethylethylcarbonylamino group, a methoxycarbonylamino group, an ethoxycarbonylamino group, a methanesulfonylamino group, an N-acetyl-N-methylamino group, an N-ethoxycarbonyl-N-methylamino group and a methanesulfonylmethylamino group.

Examples of the $CONR^9R^{10}$ group include a carbamoyl group, a methylcarbamoyl group, a dimethylcarbamoyl group, an ethylmethylcarbamoyl group, a (2-propenyl)carbamoyl group, a (2-propynyl)carbamoyl group and a 2-chloroethylcarbamoyl group.

Examples of the $C_1$-$C_4$ alkyl group represented by $R^{11}$ include a methyl group, an ethyl group, a 1-methylethyl group, a 1,1-dimethylethyl group, a propyl group and a 1-methylpropyl group.

Examples of the $C_1$-$C_4$ alkyl group represented by $R^{12}$ include a methyl group, an ethyl group, a 1-methylethyl group, a 1,1-dimethylethyl group, a propyl group and a 1-methylpropyl group.

Examples of the halogen atom represented by $R^{13}$ include a fluorine atom, a chlorine atom, a bromine atom and an iodine atom.

Examples of the $C_1$-$C_6$ alkoxy group represented by $R^{13}$ include a methoxy group, an ethoxy group, a propoxy group, an isopropoxy group, a butoxy group, an isobutoxy group, a sec-butoxy group, a tert-butoxy group, a pentyloxy group, an isopentyloxy group and a hexyloxy group.

Examples of the $C_3$-$C_6$ alkenyloxy group represented by $R^{13}$ include a 2-propenyloxy group, a 1-methyl-2-propenyloxy group, a 2-methyl-2-propenyloxy group, a 2-butenyloxy group, a 3-butenyloxy group, a 2-hexenyloxy group and a 5-hexenyloxy group.

Examples of the $C_1$-$C_6$ haloalkyl group represented by $R^{13}$ include a fluoromethyl group, a difluoromethyl group, a trifluoromethyl group, a trichloromethyl group, a chlorofluoromethyl group, a bromodifluoromethyl group, a 2-fluoroethyl group, a 2,2-difluoroethyl group, a 2,2,2-trifluoroethyl group and a 6,6,6-trifluorohexyl group.

Examples of the $C_1$-$C_6$ haloalkoxy group represented by $R^{13}$ include a trifluoromethoxy group, a difluoromethoxy group, a bromodifluoromethoxy group, a chlorodifluoromethoxy group, a fluoromethoxy group, a 2,2,2-trifluoroethoxy group, a 1,1,2,2-tetrafluoroethoxy group, a 5-chloropentyloxy group, a 4-fluoroisopentyloxy group and a 2,2-dichlorohexyloxy group.

Examples of the $C_1$-$C_3$ alkylthio group represented by $R^{13}$ include a methylthio group, an ethylthio group, a 1-methylethylthio group and a propylthio group.

Examples of the hydroxy $C_1$-$C_6$ alkyl group represented by $R^{13}$ include a hydroxymethyl group, a 1-hydroxyethyl group, a 2-hydroxyethyl group, a 1-hydroxypropyl group and a 2-hydroxypropyl group.

Examples of the $C_2$-$C_4$ alkylcarbonyloxy group represented by $R^{13}$ include an acetoxy group, an ethylcarbonyloxy group, a 1-methylethylcarbonyloxy group and a propylcarbonyloxy group.

Examples of the ($C_1$-$C_3$ alkylamino)$C_1$-$C_6$ alkyl group represented by $R^{13}$ include an N-methylaminomethyl group, an N-ethylaminomethyl group, a 1-(N-methylamino)ethyl group, a 2-(N-methylamino)ethyl group and a 1-(N-ethylamino)ethyl group.

Examples of the (di($C_1$-$C_3$ alkyl)amino)$C_1$-$C_6$ alkyl group represented by $R^{13}$ include an N,N-dimethylaminomethyl group, a 1-(N,N-dimethylamino)ethyl group, a 2-(N,N-dimethylamino)ethyl group and an N,N-diethylaminomethyl group.

Examples of the $C_2$-$C_6$ cyanoalkyl group represented by $R^{13}$ include a cyanomethyl group, a 1-cyanoethyl group and a 2-cyanoethyl group.

Examples of the $C_1$-$C_3$ alkylsulfonyl group represented by $R^{13}$ include a methanesulfonyl group and an ethanesulfonyl group.

Examples of the $C_1$-$C_4$ alkyl group represented by $R^{14}$ include a methyl group, an ethyl group, a 1-methylethyl group, a 1,1-dimethylethyl group, a propyl group and a 1-methylpropyl group.

Examples of the $C_2$-$C_5$ alkylcarbonyl group represented by $R^{14}$ include an acetyl group, an ethylcarbonyl group, a 1-methylethylcarbonyl group and a 1,1-dimethylethylcarbonyl group.

Examples of the $C_2$-$C_5$ alkoxycarbonyl group represented by $R^{14}$ include a methoxycarbonyl group, an ethoxycarbonyl group, a 1-methylethoxycarbonyl group and a 1,1-dimethylethoxycarbonyl group.

Examples of the $C_1$-$C_4$ alkylsulfonyl group represented by $R^{14}$ include a methylsulfonyl group, an ethylsulfonyl group, a 1-methylethylsulfonyl group and a 1,1-dimethylethylsulfonyl group.

Examples of the $C_1$-$C_4$ alkyl group represented by $R^{15}$ include a methyl group, an ethyl group, a 1-methylethyl group, a 1,1-dimethylethyl group, a propyl group and a 1-methylpropyl group.

Examples of the $C_2$-$C_5$ alkylcarbonyl group represented by $R^{15}$ include an acetyl group, an ethylcarbonyl group, a 1-methylethylcarbonyl group and a 1,1-dimethylethylcarbonyl group.

Examples of the $C_2$-$C_5$ alkoxycarbonyl group represented by $R^{15}$ include a methoxycarbonyl group, an ethoxycarbonyl group, a 1-methylethoxycarbonyl group and a 1,1-dimethylethoxycarbonyl group.

Examples of the $C_1$-$C_4$ alkylsulfonyl group represented by $R^{15}$ include a methylsulfonyl group, an ethylsulfonyl group, a 1-methylethylsulfonyl group and a 1,1-dimethylethylsulfonyl group.

Examples of the $NR^{14}R^{15}$ group include an amino group, a methylamino group, a dimethylamino group, an ethylamino group, an acetylamino group, a propionylamino group, a 1,1-dimethylethylcarbonylamino group, a methoxycarbonylamino group, an ethoxycarbonylamino group, a 1,1-dimethylethoxycarbonylamino group, a methanesulfonylamino group, an N-acetyl-N-methylamino group, an N-ethoxycarbonyl-N-methylamino group and a methanesulfonylmethylamino group.

In the group [a-1], examples of the $C_1$-$C_6$ alkoxy group include a methoxy group, an ethyoxy group, a propoxy group, an isopropoxy group, a butoxy group, an isobutoxy group, a sec-butoxy group, a tert-butoxy group, a pentyloxy group, an isopentyloxy group and a hexyloxy group.

Examples of the $C_3$-$C_6$ alkenyloxy group in the group [a-1] include a 2-propenyloxy group, a 1-methyl-2-propenyloxy group, a 2-methyl-2-propenyloxy group, a 2-butenyloxy group, a 3-butenyloxy group, a 2-hexenyloxy group and a 5-hexenyloxy group.

Examples of the $C_1$-$C_6$ haloalkyl group in the group [a-1] include a fluoromethyl group, a difluoromethyl group, a trifluoromethyl group, a trichloromethyl group, a chlorofluoromethyl group, a bromodifluoromethyl group, a 2-fluoroethyl group, a 2,2-difluoroethyl group, a 2,2,2-trifluoroethyl group and a 6,6,6-trifluorohexyl group.

Examples of the $C_1$-$C_6$ haloalkoxy group in the group [a-1] include a trifluoromethoxy group, a difluoromethoxy group, a bromodifluoromethoxy group, a chlorodifluoromethoxy group, a fluoromethoxy group, a 2,2,2-trifluoroethoxy group, a 1,1,2,2-tetrafluoroethoxy group, a 5-chloropentyloxy group, a 4-fluoroisopentyloxy group and a 2,2-dichlorohexyloxy group.

Examples of the $C_1$-$C_3$ alkylthio group in the group [a-1] include a methylthio group, an ethylthio group, a 1-methylethylthio group and a propylthio group.

Examples of the $C_1$-$C_3$ alkylidene group which forms a double bond with the same carbon atom forming a ring in the group [a-1] include a methylene group which forms a double bond with the same carbon atom forming a ring, an ethylidene group which forms a double bond with the same carbon atom forming a ring, an isopropylidene group which forms a double bond with the same carbon atom forming a ring and a propylidene group which forms a double bond with the same carbon atom forming a ring.

Examples of the hydroxy $C_1$-$C_6$ alkyl group in the group [a-1] include a hydroxymethyl group, a 1-hydroxyethyl group, a 2-hydroxyethyl group, a 1-hydroxypropyl group and a 2-hydroxypropyl group.

Examples of the $C_2$-$C_4$ alkylcarbonyloxy group in the group [a-1] include an acetoxy group, an ethylcarbonyloxy group, a 1-methylethylcarbonyloxy group and a propylcarbonyloxy group, Examples of the ($C_1$-$C_3$ alkylamino)$C_1$-$C_6$ alkyl group in the group [a-1] include an N-methylaminomethyl group, an N-ethylaminomethyl group, a 1-(N-methylamino)ethyl group, a 2-(N-methylamino)ethyl group and a 1-(N-ethylamino)ethyl group.

Examples of the (di($C_1$-$C_3$ alkyl)amino)$C_1$-$C_6$ alkyl in the group [a-1] include an N,N-dimethylaminomethyl group, a 1-(N,N-dimethylamino)ethyl group, a 2-(N,N-dimethylamino)ethyl group and an N,N-diethylaminomethyl group.

Examples of the $C_2$-$C_6$ cyanoalkyl group in the group [a-1] include a cyanomethyl group, a 1-cyanoethyl group and a 2-cyanoethyl group.

Examples of the $C_1$-$C_3$ alkylsulfonyl group in the group [a-1] include a methanesulfonyl group and an ethanesulfonyl group.

Examples of the $C_1$-$C_4$ alkyl group represented by $R^{16}$ include a methyl group, an ethyl group, a 1-methylethyl group, a 1,1-dimethylethyl group, a propyl group and a 1-methylpropyl group.

Examples of the $C_2$-$C_5$ alkylcarbonyl group represented by $R^{16}$ include an acetyl group, an ethylcarbonyl group, a 1-methylethylcarbonyl group and a 1,1-dimethylethylcarbonyl group, examples of the $C_2$-$C_5$ alkoxycarbonyl group include a methoxycarbonyl group, an ethoxycarbonyl group, a 1-methylethoxycarbonyl group and a 1,1-dimethylethoxycarbonyl group.

Examples of the $C_1$-$C_4$ alkylsulfonyl group represented by $R^{16}$ include a methylsulfonyl group, an ethylsulfonyl group, a 1-methylethylsulfonyl group and a 1,1-dimethylethylsulfonyl group.

Examples of the $C_1$-$C_4$ alkyl group represented by $R^{17}$ include a methyl group, an ethyl group, a 1-methylethyl group, a 1,1-dimethylethyl group, a propyl group and a 1-methylpropyl group.

Examples of the $C_2$-$C_5$ alkylcarbonyl group represented by $R^{17}$ include an acetyl group, an ethylcarbonyl group, a 1-methylethylcarbonyl group and a 1,1-dimethylethylcarbonyl group.

Examples of the $C_2$-$C_5$ alkoxycarbonyl group represented by $R^{17}$ include a methoxycarbonyl group, an ethoxycarbonyl group, a 1-methylethoxycarbonyl group and a 1,1-dimethylethoxycarbonyl group.

Examples of the $C_1$-$C_4$ alkylsulfonyl group represented by $R^{17}$ include a methylsulfonyl group, an ethylsulfonyl group, a 1-methylethylsulfonyl group and a 1,1-dimethylethylsulfonyl group.

Examples of the $NR^{16}R^{17}$ group include an amino group, a methylamino group, a dimethylamino group, an ethylamino group, an acetylamino group, a propionylamino group, a 1,1-dimethylethylcarbonylamino group, a methoxycarbonylamino group, an ethoxycarbonylamino group, a 1,1-dimethylethoxycarbonylamino group, a methanesulfonylamino group, an N-acetyl-N-methylamino group, an N-ethoxycarbonyl-N-methylamino group and a methanesulfonylmethylamino group.

In the group [a-2], examples of the halogen atom include a fluorine atom, a chlorine atom, a bromine atom and an iodine atom.

Examples of the $C_1$-$C_4$ alkyl group in the group [a-2] include a methyl group, an ethyl group, a 1-methylethyl group, a 1,1-dimethylethyl group, a propyl group and a 1-methylpropyl group.

Examples of the $C_2$-$C_4$ alkenyl group in the group [a-2] include a vinyl group, a 1-propenyl group, a 2-propenyl group, a 2-butenyl group and a 3-butenyl group.

Examples of the $C_2$-$C_4$ alkynyl group in the group [a-2] include an ethynyl group, a 1-propynyl group, a 2-propynyl group and a 3-butynyl group.

Examples of the $C_2$-$C_5$ alkoxycarbonyl group in the group [a-2] include a methoxycarbonyl group, an ethoxycarbonyl group, a 1-methylethoxycarbonyl group and a 1,1-dimethylethoxycarbonyl group.

Examples of the $C_1$-$C_6$ alkoxy group in the group [a-2] include a methoxy group, an ethoxy group, a propoxy group, an isopropoxy group, a butoxy group, an isobutoxy group, a sec-butoxy group, a tert-butoxy group, a pentyloxy group, an isopentyloxy group and a hexyloxy group.

Examples of the $C_3$-$C_6$ alkenyloxy group in the group [a-2] include a 2-propenyloxy group, a 1-methyl-2-propenyloxy group, a 2-methyl-2-propenyloxy group, a 2-butenyloxy group, a 3-butenyloxy group, a 2-hexenyloxy group and a 5-hexenyloxy group.

Examples of the $C_1$-$C_6$ haloalkyl group in the group [a-1] include a fluoromethyl group, a difluoromethyl group, a trifluoromethyl group, a trichloromethyl group, a chlorofluoromethyl group, a bromodifluoromethyl group, a 2-fluoroethyl group, a 2,2-difluoroethyl group, a 2,2,2-trifluoroethyl group and a 6,6,6-trifluorohexyl group.

Examples of the $C_1$-$C_6$ haloalkoxy group in the group [a-2] include a trifluoromethoxy group, a difluoromethoxy group, a bromodifluoromethoxy group, a chlorodifluoromethoxy group, a fluoromethoxy group, a 2,2,2-trifluoroethoxy group, a 1,1,2,2-tetrafluoroethoxy group, a 5-chloropentyloxy group, a 4-fluoroisopentyloxy group and a 2,2-dichlorohexyloxy group.

Examples of the $C_1$-$C_3$ alkylthio group in the group [a-2] include a methylthio group, an ethylthio group, a 1-methylethylthio group and a propylthio group.

Examples of the $C_1$-$C_3$ alkylidene group which forms a double bond with the same carbon atom forming a ring in the group [a-2] include a methylene group which forms a double bond with the same carbon atom forming a ring, an ethylidene group which forms a double bond with the same carbon atom forming a ring, an isopropylidene group which forms a double bond with the same carbon atom forming a ring and a propylidene group which forms a double bond with the same carbon atom forming a ring.

Examples of the hydroxy $C_1$-$C_6$ alkyl group in the group [a-2] include a hydroxymethyl group, a 1-hydroxyethyl group, a 2-hydroxyethyl group, a 1-hydroxypropyl group and a 2-hydroxypropyl group, Examples of the $C_2$-$C_4$ alkylcarbonyloxy group in the group [a-2] include an acetoxy group, an ethylcarbonyloxy group, a 1-methylethylcarbonyloxy group and a propylcarbonyloxy group, Examples of the ($C_1$-$C_3$ alkylamino)$C_1$-$C_6$ alkyl group in the group [a-2] include an N-methylaminomethyl group, an N-ethylaminomethyl group, a 1-(N-methylamino)ethyl group, a 2-(N-methylamino)ethyl group and a 1-(N-ethylamino)ethyl group.

Examples of the (di($C_1$-$C_3$ alkyl)amino)$C_1$-$C_6$ alkyl group in the group [a-2] include an N,N-dimethylaminomethyl group, a 1-(N,N-dimethylamino)ethyl group, a 2-(N,N-dimethylamino)ethyl group and an N,N-diethylaminomethyl group.

Examples of the $C_2$-$C_6$ cyanoalkyl group in the group [a-2] include a cyanomethyl group, a 1-cyanoethyl group and a 2-cyanoethyl group.

Examples of the $C_1$-$C_3$ alkylsulfonyl group in the group [a-2] include a methanesulfonyl group and an ethanesulfonyl group.

Examples of the $C_1$-$C_4$ alkyl group represented by $R^{18}$ include a methyl group, an ethyl group, a 1-methylethyl group, a 1,1-dimethylethyl group, a propyl group and a 1-methylpropyl group.

Examples of the $C_2$-$C_5$ alkylcarbonyl group represented by $R^{18}$ include an acetyl group, an ethylcarbonyl group, a 1-methylethylcarbonyl group and a 1,1-dimethylethylcarbonyl group.

Examples of the $C_2$-$C_5$ alkoxycarbonyl group represented by $R^{18}$ include a methoxycarbonyl group, an ethoxycarbonyl group, a 1-methylethoxycarbonyl group and a 1,1-dimethylethoxycarbonyl group.

Examples of the $C_1$-$C_4$ alkylsulfonyl group represented by $R^{18}$ include a methylsulfonyl group, an ethylsulfonyl group, a 1-methylethylsulfonyl group and a 1,1-dimethylethylsulfonyl group.

Examples of the $C_1$-$C_4$ alkyl group represented by $R^{19}$ include a methyl group, an ethyl group, a 1-methylethyl group, a 1,1-dimethylethyl group, a propyl group and a 1-methylpropyl group.

Examples of the $C_2$-$C_5$ alkylcarbonyl group represented by $R^{19}$ include an acetyl group, an ethylcarbonyl group, a 1-methylethylcarbonyl group and a 1,1-dimethylethylcarbonyl group.

Examples of the $C_2$-$C_5$ alkoxycarbonyl group represented by $R^{19}$ include a methoxycarbonyl group, an ethoxycarbonyl group, a 1-methylethoxycarbonyl group and a 1,1-dimethylethoxycarbonyl group.

Examples of the $C_1$-$C_4$ alkylsulfonyl group represented by $R^{19}$ include a methylsulfonyl group, an ethylsulfonyl group, a 1-methylethylsulfonyl group and a 1,1-dimethylethylsulfonyl group.

Examples of the $NR^{18}R^{19}$ group include an amino group, a methylamino group, a dimethylamino group, an ethylamino group, an acetylamino group, a propionylamino group, a 1,1-dimethylethylcarbonylamino group, a methoxycarbonylamino group, an ethoxycarbonylamino group, a 1,1-dimethylethoxycarbonylamino group, a methanesulfonylamino group, an N-acetyl-N-methylamino group, an N-ethoxycarbonyl-N-methylamino group and a methanesulfonylmethylamino group.

Examples of the $C_3$-$C_6$ cycloalkyl group in the $C_3$-$C_6$ cycloalkyl group substituted with at least one group selected from the group [a-1] which is represented by $Cy^1$ include a cyclopropyl group, a cyclobutyl group, a cyclopentyl group and a cyclohexyl group.

Examples of the $C_3$-$C_6$ cycloalkenyl group in the $C_3$-$C_6$ cycloalkenyl group optionally substituted with at least one group selected from the group [a-1] which is represented by $Cy^1$ include a 2-cyclopropenyl group, a 1-cyclobutenyl group, a 2-cyclobutenyl group, a 1-cyclopentenyl group, a 2-cyclopentenyl group, a 3-cyclopentenyl group, a 1-cyclohexenyl group, a 2-cyclohexenyl group and a 3-cyclohexenyl group.

Examples of the $C_3$-$C_6$ cycloalkyl group which is optionally substituted with at least one group selected from the group [a-1] and in which one of methylenes forming the ring is replaced with a carbonyl group, which is represented by $Cy^1$, include a 2-oxocyclopropyl group, a 2-oxocyclobutyl group, a 3-oxocyclobutyl group, a 2-oxocyclopentyl group, a 3-oxocyclopentyl group, a 2-oxocyclohexyl group, a 3-oxocyclohexyl group and a 4-oxocyclohexyl group.

Examples of the $C_3$-$C_6$ hydroxyiminocycloalkyl group in the $C_3$-$C_6$ hydroxyiminocycloalkyl group optionally substituted with at least one group selected from the group [a-1] which is represented by $Cy^1$ include a 2-hydroxyiminocyclopropyl group, 2-hydroxyiminocyclobutyl group, a 3-hydroxyiminocyclobutyl group, a 2-hydroxyiminocyclopentyl group, a 3-hydroxyiminocyclopentyl group, a 2-hydroxyiminocyclohexyl group, a 3-hydroxyiminocyclohexyl group and a 4-hydroxyiminocyclohexyl group.

Examples of the $C_3$-$C_6$ cycloalkyl group in the $C_3$-$C_6$ cycloalkyl group optionally substituted with at least one group selected from the group [a-2] represented by $Cy^2$ include a cyclopropyl group, a cyclobutyl group, a cyclopentyl group and a cyclohexyl group.

Examples of the $C_3$-$C_6$ cycloalkenyl group in the $C_3$-$C_6$ cycloalkenyl group optionally substituted with at least one group selected from the group [a-2] represented by $Cy^2$ include a 2-cyclopropenyl group, a 1-cyclobutenyl group, a 2-cyclobutenyl group, a 1-cyclopentenyl group, a 2-cyclopentenyl group, a 3-cyclopentenyl group, a 1-cyclohexenyl group, a 2-cyclohexenyl group and a 3-cyclohexenyl group.

Examples of the $C_3$-$C_6$ cycloalkyl group which is optionally substituted with at least one group selected from the group [a-2] and in which one of methylenes forming the ring is replaced with a carbonyl group, represented by $Cy^2$, include a 2-oxocyclopropyl group, a 2-oxocyclobutyl group, a 3-oxocyclobutyl group, a 2-oxocyclopentyl group, a 3-oxocyclopentyl group, a 2-oxocyclohexyl group, a 3-oxocyclohexyl group and a 4-oxocyclohexyl group.

Examples of the $C_3$-$C_6$ hydroxyiminocycloalkyl group in the $C_3$-$C_6$ hydroxyiminocycloalkyl group optionally substituted with at least one group selected from the group [a-1] represented by $Cy^2$ include a 2-hydroxyiminocyclopropyl group, a 2-hydroxyiminocyclobutyl group, a 3-hydroxyiminocyclobutyl group, a 2-hydroxyiminocyclopentyl group, a 3-hydroxyiminocyclopentyl group, a 2-hydroxyiminocyclohexyl group, a 3-hydroxyiminocyclohexyl group and a 4-hydroxyiminocyclohexyl group.

Examples of the group represented by $A^2$-$Cy^1$ include specifically a {1-(hydroxymethyl)cyclohexyl}methyl group, a {1-(hydroxymethyl)cyclobutyl}methyl group, a {1-(hydroxymethyl)cyclopentyl}methyl group, a {1-(hydroxymethyl)cyclopropyl}methyl group, a (3-cyclohexenyl)methyl group, a (2-cyclohexenyl)methyl group, a (1-cyclohexenyl)methyl group, a {1-(dimethylamino)cyclohexyl}methyl group, a {1-(dimethylamino)cyclopentyl}methyl group, a {1-(dimethylamino)cyclobutyl}methyl group, a {1-(dimethylamino)cyclopropyl}methyl group, a (1-acetoxycyclohexyl)methyl group, a (1-acetoxycyclopentyl)methyl group, a (1-acetoxycyclobutyl)methyl group, a (1-acetoxycyclopropyl)methyl group, a (2-acetoxycyclohexyl)methyl group, a 2-cyclohexenyl group, a 3-cyclohexenyl group, a 2-methoxycyclohexyl group, a 2-methoxycyclopentyl group, a 2-methoxycyclobutyl group, a 3-methoxycyclohexyl group, a 4-methoxycyclohexyl group, a (2-methoxycyclohexyl)methyl group, a (1-methoxycyclohexyl)methyl group, a 2-acetoxycyclohexyl group, a 2-acetoxycyclopentyl group, a 2-acetoxycyclobutyl group, a 2-methylthiocyclohexyl group, a 2-methylthiocyclopentyl group, a 2-methylthiocyclobutyl group, a 2-(1,1-dimethylethoxycarbonylamino)cyclohexyl group, a 2-(1,1-dimethylethoxycarbonylamino)cyclopentyl group, a 2-(1,1-dimethylethoxycarbonylamino)cyclobutyl group, a 2-aminocyclohexyl group, a 2-aminocyclopentyl group, a 2-aminocyclobutyl group, a 2-acetylaminocyclohexyl group, a 2-acetylaminocyclopentyl group, a 2-acetylaminocyclobutyl group, a 2-dimethylaminocyclohexyl group, a 2-dimethylaminocyclopentyl group, a 2-dimethylaminocyclobutyl group, a 2-phenylcyclohexyl group, a 2-phenylcyclopentyl group, a 2-phenylcyclobutyl group, a 2-benzylcyclohexyl group, a 2-benzylcyclopentyl group, a 2-benzylcyclobutyl group, a 2-trifluoromethylcyclohexyl group, a 2-trifluoromethylcyclopentyl group, a 2-trifluoromethylcyclobutyl group, a 2-trifluoromethylcyclopropyl group, a 2-hydroxymethylcyclohexyl group, a 2-hydroxymethylcyclopentyl group, a 2-hydroxymethylcyclobutyl group, a 2-methylenecyclohexyl group, a 3-methylenecyclohexyl group, a 4-methylenecyclohexyl group, a 2-oxocyclohexyl group, a 3-oxocyclohexyl group, a 4-oxocyclohexyl group, a 2-oxocyclopentyl group, a 3-oxocyclopentyl group, a 2-hydroxyiminocyclohexyl group, and a 2-hydroxyiminocyclopentyl group.

Examples of the group represented by $A^3$-$Cy^2$ include specifically a 1-cyclohexyl-2,2,2-trifluoroethyl group, a 1-cyclopentyl-2,2,2-trifluoroethyl group, a 1-cyclobutyl-2,2,2-trifluoroethyl group, a 1-cyano-1-cyclohexylmethyl group, a 1-cyano-1-cyclopentylmethyl group, a 1-cyano-1-cyclobutylmethyl group, a 1-vinyl-1-cyclohexylmethyl group, a 1-vinyl-1-cyclopentylmethyl group, a 1-vinyl-1-cyclobutylmethyl group, a 1-methoxycarbonyl-1-cyclohexylmethyl group, a 1-methoxycarbonyl-1-cyclopentylmethyl group, and a 1-methoxycarbonyl-1-cyclobutylmethyl group.

Examples of the compound of the present invention include the following embodiments:

an amide compound of the formula (1), wherein Z is an oxygen atom, $X^1$ is a fluorine atom, and $X^2$ is a hydrogen atom;

an amide compound of the formula (1), wherein Z is an oxygen atom, $X^1$ is a fluorine atom, and $X^2$ is a fluorine atom;

an amide compound of the formula (1), wherein Z is an oxygen atom, $X^1$ is a fluorine atom, and $X^2$ is a chlorine atom;

an amide compound of the formula (1), wherein Z is an oxygen atom, $X^1$ is a fluorine atom, and $X^2$ is a bromine atom;

an amide compound of the formula (1), wherein Z is an oxygen atom, $X^1$ is a fluorine atom, and $X^2$ is an iodine atom;

an amide compound of the formula (1), wherein Z is an oxygen atom, $X^1$ is a fluorine atom, and $X^2$ is a $C_1$-$C_4$ alkyl group;

an amide compound of the formula (1), wherein Z is an oxygen atom, $X^1$ is a fluorine atom, and $X^2$ is a $C_2$-$C_4$ alkenyl group;

an amide compound of the formula (1), wherein Z is an oxygen atom, $X^1$ is a fluorine atom, and $X^2$ is a $C_2$-$C_4$ alkynyl group;

an amide compound of the formula (1), wherein Z is an oxygen atom, $X^1$ is a fluorine atom, and $X^2$ is a $C_1$-$C_4$ haloalkyl group;

an amide compound of the formula (1), wherein Z is an oxygen atom, $X^1$ is a fluorine atom, and $X^2$ is a $C_1$-$C_4$ alkoxy group;

an amide compound of the formula (1), wherein Z is an oxygen atom, $X^1$ is a fluorine atom, and $X^2$ is a $C_1$-$C_4$ alkylthio group;

an amide compound of the formula (1), wherein Z is an oxygen atom, $X^1$ is a fluorine atom, and $X^2$ is a hydroxy $C_1$-$C_4$ alkyl group;

an amide compound of the formula (1), wherein Z is an oxygen atom, $X^1$ is a fluorine atom, and $X^2$ is a nitro group;

an amide compound of the formula (1), wherein Z is an oxygen atom, $X^1$ is a fluorine atom, and $X^2$ is a cyano group;

an amide compound of the formula (1), wherein Z is an oxygen atom, $X^1$ is a fluorine atom, and $X^2$ is a formyl group;

an amide compound of the formula (1), wherein Z is an oxygen atom, $X^1$ is a fluorine atom, and $X^2$ is an $NR^1R^2$ group;

an amide compound of the formula (1), wherein Z is an oxygen atom, $X^1$ is a fluorine atom, and $X^2$ is a $CO_2R^3$ group;

an amide compound of the formula (1), wherein Z is an oxygen atom, $X^1$ is a fluorine atom, and $X^2$ is a $CONR^4R^5$ group;

an amide compound of the formula (1), wherein Z is an oxygen atom, $X^1$ is a fluorine atom, and $X^2$ is a phenyl group optionally substituted with at least one group selected from the group consisting of a methyl group, a halogen atom, a cyano group and a nitro group;

an amide compound of the formula (1), wherein Z is an oxygen atom, $X^1$ is a methoxy group, and $X^2$ is a hydrogen atom;

an amide compound of the formula (1), wherein Z is an oxygen atom, $X^1$ is a methoxy group, and $X^2$ is a fluorine atom;

an amide compound of the formula (1), wherein Z is an oxygen atom, $X^1$ is a methoxy group, and $X^2$ is a chlorine atom;

an amide compound of the formula (1), wherein Z is an oxygen atom, $X^1$ is a methoxy group, and $X^2$ is a bromine atom;

an amide compound of the formula (1), wherein Z is an oxygen atom, $X^1$ is a methoxy group, and $X^2$ is an iodine atom;

an amide compound of the formula (1), wherein Z is an oxygen atom, $X^1$ is a methoxy group, and $X^2$ is a $C_1$-$C_4$ alkyl group;

an amide compound of the formula (1), wherein Z is an oxygen atom, $X^1$ is a methoxy group, and $X^2$ is a $C_2$-$C_4$ alkenyl group;

an amide compound of the formula (1), wherein Z is an oxygen atom, $X^1$ is a methoxy group, and $X^2$ is a $C_2$-$C_4$ alkynyl group;

an amide compound of the formula (1), wherein Z is an oxygen atom, $X^1$ is a methoxy group, and $X^2$ is a $C_1$-$C_4$ haloalkyl group;

an amide compound of the formula (1), wherein Z is an oxygen atom, $X^1$ is a methoxy group, and $X^2$ is a $C_1$-$C_4$ alkoxy group;

an amide compound of the formula (1), wherein Z is an oxygen atom, $X^1$ is a methoxy group, and $X^2$ is a $C_1$-$C_4$ alkylthio group;

an amide compound of the formula (1), wherein Z is an oxygen atom, $X^1$ is a methoxy group, and $X^2$ is a hydroxy $C_1$-$C_4$ alkyl group;

an amide compound of the formula (1), wherein Z is an oxygen atom, $X^1$ is a methoxy group, and $X^2$ is a nitro group;

an amide compound of the formula (1), wherein Z is an oxygen atom, $X^1$ is a methoxy group, and $X^2$ is a cyano group;

an amide compound of the formula (1), wherein Z is an oxygen atom, $X^1$ is a methoxy group, and $X^2$ is a formyl group;

an amide compound of the formula (1), wherein Z is an oxygen atom, $X^1$ is a methoxy group, and $X^2$ is an $NR^1R^2$ group;

an amide compound of the formula (1), wherein Z is an oxygen atom, $X^1$ is a methoxy group, and $X^2$ is a $CO_2R^3$ group;

an amide compound of the formula (1), wherein Z is an oxygen atom, $X^1$ is a methoxy group, and $X^2$ is a $CONR^4R^5$ group;

an amide compound of the formula (1), wherein Z is an oxygen atom, $X^1$ is a methoxy group, and $X^2$ is a phenyl group optionally substituted with at least one group selected from the group consisting of the a methyl group, a halogen atom, a cyano group and a nitro group;

an amide compound of the formula (1), wherein Z is an oxygen atom, $X^1$ is a fluorine atom, and $X^3$ is a fluorine atom;

an amide compound of the formula (1), wherein Z is an oxygen atom, $X^1$ is a fluorine atom, and $X^3$ is a chlorine atom;

an amide compound of the formula (1), wherein Z is an oxygen atom, $X^1$ is a fluorine atom, and $X^3$ is a bromine atom;

an amide compound of the formula (1), wherein Z is an oxygen atom, $X^1$ is a fluorine atom, and $X^3$ is an iodine atom;

an amide compound of the formula (1), wherein Z is an oxygen atom, $X^1$ is a fluorine atom, and $X^3$ is a $C_1$-$C_4$ alkyl group;

an amide compound of the formula (1), wherein Z is an oxygen atom, $X^1$ is a fluorine atom, and $X^3$ is a $C_2$-$C_4$ alkenyl group;

an amide compound of the formula (1), wherein Z is an oxygen atom, $X^1$ is a fluorine atom, and $X^3$ is a $C_2$-$C_4$ alkynyl group;

an amide compound of the formula (1), wherein Z is an oxygen atom, $X^1$ is a fluorine atom, and $X^3$ is a $C_1$-$C_4$ haloalkyl group;

an amide compound of the formula (1), wherein Z is an oxygen atom, $X^1$ is a fluorine atom, and $X^3$ is a $C_1$-$C_4$ alkoxy group;

an amide compound of the formula (1), wherein Z is an oxygen atom, $X^1$ is a fluorine atom, and $X^3$ is a $C_1$-$C_4$ alkylthio group;

an amide compound of the formula (1), wherein Z is an oxygen atom, $X^1$ is a fluorine atom, and $X^3$ is a nitro group;

an amide compound of the formula (1), wherein Z is an oxygen atom, $X^1$ is a fluorine atom, and $X^3$ is a cyano group;

an amide compound of the formula (1), wherein Z is an oxygen atom, $X^1$ is a fluorine atom, and $X^3$ is a formyl group;

an amide compound of the formula (1), wherein Z is an oxygen atom, $X^1$ is a fluorine atom, and $X^3$ is an $NR^6R^7$ group;

an amide compound of the formula (1), wherein Z is an oxygen atom, $X^1$ is a fluorine atom, and $X^3$ is a $CO_2R^8$ group;

an amide compound of the formula (1), wherein Z is an oxygen atom, $X^1$ is a fluorine atom, and $X^3$ is a $CONR^9R^{10}$ group;

an amide compound of the formula (1), wherein Z is an oxygen atom, $X^1$ is a fluorine atom, and $X^3$ is a phenyl group optionally substituted with at least one group selected from the group consisting of a methyl group, a halogen atom, a cyano group and a nitro group;

an amide compound of the formula (1), wherein Z is an oxygen atom, $X^1$ is a methoxy group, and $X^3$ is a fluorine atom;

an amide compound of the formula (1), wherein Z is an oxygen atom, $X^1$ is a methoxy group, and $X^3$ is a chlorine atom;

an amide compound of the formula (1), wherein Z is an oxygen atom, $X^1$ is a methoxy group, and $X^3$ is a bromine atom;

an amide compound of the formula (1), wherein Z is an oxygen atom, $X^1$ is a methoxy group, and $X^3$ is an iodine atom;

an amide compound of the formula (1), wherein Z is an oxygen atom, $X^1$ is a methoxy group, and $X^3$ is a $C_1$-$C_4$ alkyl group;

an amide compound of the formula (1), wherein Z is an oxygen atom, $X^1$ is a methoxy group, and $X^3$ is a $C_2$-$C_4$ alkenyl group;

an amide compound of the formula (1), wherein Z is an oxygen atom, $X^1$ is a methoxy group, and $X^3$ is a $C_2$-$C_4$ alkynyl group;

an amide compound of the formula (1), wherein Z is an oxygen atom, $X^1$ is a methoxy group, and $X^3$ is a $C_1$-$C_4$ haloalkyl group;

an amide compound of the formula (1), wherein Z is an oxygen atom, $X^1$ is a methoxy group, and $X^3$ is a $C_1$-$C_4$ alkoxy group;

an amide compound of the formula (1), wherein Z is an oxygen atom, $X^1$ is a methoxy group, and $X^3$ is a $C_1$-$C_4$ alkylthio group;

an amide compound of the formula (1), wherein Z is an oxygen atom, $X^1$ is a methoxy group, and $X^3$ is a nitro group;

an amide compound of the formula (1), wherein Z is an oxygen atom, $X^1$ is a methoxy group, and $X^3$ is a cyano group;

an amide compound of the formula (1), wherein Z is an oxygen atom, $X^1$ is a methoxy group, and $X^3$ is a formyl group;

an amide compound of the formula (1), wherein Z is an oxygen atom, $X^1$ is a methoxy group, and $X^3$ is an $NR^1R^2$ group;

an amide compound of the formula (1), wherein Z is an oxygen atom, $X^1$ is a methoxy group, and $X^3$ is a $CO_2R^3$ group;

an amide compound of the formula (1), wherein Z is an oxygen atom, $X^1$ is a methoxy group, and $X^3$ is a $CONR^4R^5$ group;

an amide compound of the formula (1), wherein Z is an oxygen atom, $X^1$ is a methoxy group, and $X^3$ is a phenyl group optionally substituted with at least one group selected from the group consisting of a methyl group, a halogen atom, a cyano group and a nitro group;

an amide compound of the formula (1), wherein Z is an oxygen atom;

an amide compound of the formula (1), wherein $X^1$ is a fluorine atom;

an amide compound of the formula (1), wherein $X^1$ is a methoxy group;

an amide compound of the formula (1), wherein Z is an oxygen atom, and $X^1$ is a fluorine atom;

an amide compound of the formula (1), wherein Z is an oxygen atom, and $X^1$ is a methoxy group;

an amide compound of the formula (1), wherein $X^2$ is a hydrogen atom, a halogen atom or a $C_1$-$C_4$ alkyl group;

an amide compound of the formula (1), wherein $X^2$ is a hydrogen atom;

an amide compound of the formula (1), wherein $X^2$ is a halogen atom;

an amide compound of the formula (1), wherein $X^2$ is a fluorine atom;

an amide compound of the formula (1), wherein $X^2$ is a hydrogen atom, or a fluorine atom;

an amide compound of the formula (1), wherein $X^2$ is a $C_1$-$C_4$ alkyl group;

an amide compound of the formula (1), wherein Z is an oxygen atom, and $X^2$ is a hydrogen atom, a halogen atom or a $C_1$-$C_4$ alkyl group;

an amide compound of the formula (1), wherein Z is an oxygen atom, and $X^2$ is a hydrogen atom;

an amide compound of the formula (1), wherein Z is an oxygen atom, and $X^2$ is a halogen atom;

an amide compound of the formula (1), wherein Z is an oxygen atom, and $X^2$ is a fluorine atom;

an amide compound of the formula (1), wherein Z is an oxygen atom, and $X^2$ is a hydrogen atom or a fluorine atom;

an amide compound of the formula (1), wherein Z is an oxygen atom, and $X^2$ is a $C_1$-$C_4$ alkyl group;

an amide compound of the formula (1), wherein $X^3$ is a halogen atom;

an amide compound of the formula (1), wherein $X^3$ is a fluorine atom;

an amide compound of the formula (1), wherein $X^3$ is a chlorine atom;

an amide compound of the formula (1), wherein Z is an oxygen atom, and $X^3$ is a halogen atom;

an amide compound of the formula (1), wherein Z is an oxygen atom, and $X^3$ is a fluorine atom;

an amide compound of the formula (1), wherein Z is an oxygen atom, and $X^3$ is a chlorine atom;

an amide compound of the formula (1), wherein A is $A^1$-$CR^{11}R^{12}R^{13}$;

an amide compound of the formula (1), wherein A is $A^1$-$CR^{11}R^{12}R^{13}$, and $R^{13}$ is a fluorine atom, an amino group or a hydroxyl group;

an amide compound of the formula (1), wherein A is $A^1$-$CR^{11}R^{12}R^{13}$, and $R^{13}$ is an amino group or a hydroxyl group;

an amide compound of the formula (1), wherein A is $A^1$-$CR^{11}R^{12}R^{13}$, $A^1$ is a $CH_2$ group or a $CH(CH_3)$ group, and $R^{13}$ is an amino group or a hydroxyl group;

an amide compound of the formula (1), wherein A is $A^1$-$CR^{11}R^{12}R^{13}$, and $R^{13}$ is a halogen atom, a hydroxyl group, a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a hydroxy $C_1$-$C_6$ alkyl group, a $C_2$-$C_4$ alkylcarbonyloxy group, a (di($C_1$-$C_3$ alkyl)amino)$C_1$-$C_6$ alkyl group, a carbamoyl group, a formyl group, a $C_2$-$C_6$ cyanoalkyl group, a $C_1$-$C_3$ alkylsulfonyl group or a phenoxy group;

an amide compound of the formula (1), wherein A is $A^1$-$CR^{11}R^{12}R^{13}$, and $R^{13}$ is a halogen atom, a hydroxyl group, a $C_1$-$C_6$ alkoxy group, a $C_3$-$C_6$ alkenyloxy group, a $C_1$-$C_6$ haloalkyl group, a $C_1$-$C_6$ haloalkoxy group, a $C_1$-$C_3$ alkylthio group, a hydroxy $C_1$-$C_6$ alkyl group, a $C_2$-$C_4$ alkylcarbonyloxy group, a (di($C_1$-$C_3$ alkyl)amino)$C_1$-$C_6$ alkyl group, a carbamoyl group, a formyl group, a $C_2$-$C_6$ cyanoalkyl group, a $C_1$-$C_3$ alkylsulfonyl group or a phenoxy group;

an amide compound of the formula (1), wherein A is $A^1$-$CR^{11}R^{12}R^{13}$, and $R^{13}$ is a halogen atom, a hydroxyl group, a $C_1$-$C_6$ alkoxy group, a $C_3$-$C_6$ alkenyloxy group, a $C_1$-$C_6$ haloalkyl group, a $C_1$-$C_6$ haloalkoxy group, a $C_1$-$C_3$ alkylthio group, a hydroxy $C_1$-$C_6$ alkyl group, or a $C_2$-$C_4$ alkylcarbonyloxy group;

an amide compound of the formula (1), wherein A is $A^1$-$CR^{11}R^{12}R^{13}$, $A^1$ is a $CH_2$ group or a $CH(CH_3)$ group, and $R^{13}$ is a hydroxyl group;

an amide compound of the formula (1), wherein A is $A^1$-$CR^{11}R^{12}R^{13}$, and $R^{13}$ is a hydroxyl group;

an amide compound of the formula (1), wherein A is $A^2$-$Cy^1$;

an amide compound of the formula (1), wherein A is $A^2$-$Cy^1$, and $A^2$ is a single bond;

an amide compound of the formula (1), wherein A is $A^2$-$Cy^1$, and $A^2$ is a $CH_2$ group;

an amide compound of the formula (1), wherein A is $A^2$-$Cy^1$, and $A^2$ is a $CH(CH_3)$ group;

an amide compound of the formula (1), wherein A is $A^2$-$Cy^1$, $A^2$ is a single bond, a $CH_2$ group or a $CH(CH_3)$ group, and $Cy^1$ is a $C_3$-$C_6$ cycloalkyl group substituted with at least one group selected from the group [a-1];

an amide compound of the formula (1), wherein A is $A^2$-$Cy^1$, $A^2$ is a single bond, a $CH_2$ group or a $CH(CH_3)$ group, and $Cy^1$ is a $C_3$-$C_6$ cycloalkyl group substituted with a group selected from the group consisting of a $C_1$-$C_6$ alkoxy group, a $C_1$-$C_6$ haloalkyl group, a $C_1$-$C_3$ alkylthio group, a $C_1$-$C_3$ alkylidene group which forms a double bond with the same carbon atom forming a ring, a hydroxy $C_1$-$C_6$ alkyl group, a $C_1$-$C_3$ alkylcarbonyloxy group and an $NR^{14}R^{15}$ group;

an amide compound of the formula (1), wherein A is $A^2$-$Cy^1$, $A^2$ is a single bond, a $CH_2$ group or a $CH(CH_3)$ group, and $Cy^1$ is a cyclohexyl group substituted with a group selected from the group consisting of a $C_1$-$C_6$ alkoxy group, a $C_1$-$C_6$ haloalkyl group, a $C_1$-$C_3$ alkylthio group, a $C_1$-$C_3$ alkylidene group which forms a double bond with the same carbon atom forming a ring, a hydroxy $C_1$-$C_6$ alkyl group, a $C_1$-$C_3$ alkylcarbonyloxy group and an $NR^{14}R^{15}$ group;

an amide compound of the formula (1), wherein A is $A^2$-$Cy^1$, $A^2$ is a single bond, a $CH_2$ group or a $CH(CH_3)$ group, and $Cy^1$ is a $C_3$-$C_6$ cycloalkyl group substituted with a group selected from the group consisting of a methoxy group, a trifluoromethyl group, a methylthio group, a methylene group which forms a double bond with the same carbon atom forming a ring, a hydroxymethyl group, an alkoxy group, an amino group, a methylamino group and a dimethylamino group;

an amide compound of the formula (1), wherein A is $A^2$-$Cy^1$, $A^2$ is a single bond, a $CH_2$ group or a $CH(CH_3)$ group, and $Cy^1$ is a cyclohexyl group substituted with a group selected from the group consisting of a $C_1$-$C_6$ alkoxy group, a $C_1$-$C_6$ haloalkyl group, a hydroxy $C_1$-$C_6$ alkyl group and a $C_1$-$C_3$ alkylcarbonyloxy group;

an amide compound of the formula (1), wherein A is $A^2$-$Cy^1$, $A^2$ is a single bond, a $CH_2$ group or a $CH(CH_3)$ group, and $Cy^1$ is a cyclopentyl group substituted with a group selected from the group consisting of a $C_1$-$C_6$ alkoxy group, a $C_1$-$C_6$ haloalkyl group, a hydroxy $C_1$-$C_6$ alkyl group and a $C_1$-$C_3$ alkylcarbonyloxy group;

an amide compound of the formula (1), wherein A is $A^2$-$Cy^1$, $A^2$ is a single bond, a $CH_2$ group or a $CH(CH_3)$ group, and $Cy^1$ is a cyclobutyl group substituted with a group selected from the group consisting of a $C_1$-$C_6$ alkoxy group, a $C_1$-$C_6$ haloalkyl group, a hydroxy $C_1$-$C_6$ alkyl group and a $C_1$-$C_3$ alkylcarbonyloxy group;

an amide compound of the formula (1), wherein A is $A^2$-$Cy^1$, $A^2$ is a single bond, a $CH_2$ group or a $CH(CH_3)$ group, and $Cy^1$ is a cyclohexyl group substituted with a group selected from the group consisting of a methoxy group, a trifluoromethyl group and a hydroxymethyl group;

an amide compound of the formula (1), wherein A is $A^2$-$Cy^1$, $A^2$ is a single bond, a $CH_2$ group or a $CH(CH_3)$ group, and $Cy^1$ is a $C_3$-$C_6$ cycloalkyl group substituted with at least one group selected from the group consisting of a $C_1$-$C_6$ alkoxy group, a $C_1$-$C_6$ haloalkyl group, a hydroxy $C_1$-$C_6$ alkyl group and a $C_2$-$C_4$ alkylcarbonyloxy group;

an amide compound of the formula (1), wherein A is $A^2$-$Cy^1$, and $Cy^1$ is a $C_3$-$C_6$ cycloalkyl group substituted with at least one group selected from the following group [b-1], wherein the group [b-1] consists of:
a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a $C_1$-$C_3$ alkylidene group which forms a double bond with the same carbon atom forming a ring, a hydroxy $C_1$-$C_6$ alkyl group, a $C_2$-$C_4$ alkylcarbonyloxy group, a (di($C_1$-$C_3$ alkyl)amino)$C_1$-$C_6$ alkyl group, a carbamoyl group, a formyl group, a $C_2$-$C_6$ cyanoalkyl group, a $C_1$-$C_3$ alkylsulfonyl group and a phenoxy group;

an amide compound of the formula (1), wherein A is $A^2$-$Cy^1$, $A^2$ is a single bond, a $CH_2$ group or a $CH(CH_3)$ group, and $Cy^1$ is a $C_3$-$C_6$ cycloalkyl group substituted with at least one group selected from the above group [b-1];

an amide compound of the formula (1), wherein $Cy^1$ is a $C_3$-$C_6$ cycloalkyl group substituted with at least one group selected from the group consisting of a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a $C_1$-$C_3$ alkylidene group which forms a double bond with the same carbon atom forming a ring, a hydroxy $C_1$-$C_6$ alkyl group, a $C_2$-$C_4$ alkylcarbonyloxy group, a (di($C_1$-$C_3$ alkyl)amino)$C_1$-$C_6$ alkyl group, a carbamoyl group, a formyl group, a $C_2$-$C_6$ cycloalkyl group, a $C_1$-$C_3$ alkylsulfonyl group and a phenoxy group;

an amide compound of the formula (1), wherein $Cy^1$ is a $C_3$-$C_6$ cycloalkyl group substituted with at least one group selected from the group consisting of a $C_1$-$C_6$ alkoxy group, a $C_3$-$C_6$ alkenyloxy group, a $C_1$-$C_6$ haloalkyl group, a $C_1$-$C_6$ haloalkoxy group, a $C_1$-$C_3$ alkylthio group, a $C_1$-$C_3$ alkylidene group which forms a double bond with the same carbon atom forming a ring, a hydroxy $C_1$-$C_6$ alkyl group, a $C_2$-$C_4$ alkylcarbonyloxy group, a (di($C_1$-$C_3$ alkyl)amino)$C_1$-$C_6$ alkyl group, a $C_2$-$C_6$ cyanoalkyl group and a phenoxy group;

an amide compound of the formula (1), wherein $Cy^1$ is a $C_3$-$C_6$ cycloalkyl group substituted with at least one group selected from the group consisting of a $C_1$-$C_6$ alkoxy group, a $C_1$-$C_6$ haloakly group, a $C_1$-$C_3$ alkylthio group, a $C_1$-$C_3$ alkylidene group which forms a double bond with the same carbon atom forming a ring, a hydroxy $C_1$-$C_6$ alkyl group and a $C_2$-$C_4$ alkylcarbonyloxy group;

an amide compound of the formula (1), wherein $Cy^1$ is a cyclohexyl group substituted with at least one group selected from the group consisting of a $C_1$-$C_6$ alkoxy group, a $C_1$-$C_6$ haloalkyl group, a $C_1$-$C_3$ alkylthio group, a $C_1$-$C_3$ alkylidene group which forms a double bond with the same carbon atom forming a ring, a hydroxy $C_1$-$C_6$ alkyl group and a $C_2$-$C_4$ alkylcarbonyloxy group;

an amide compound of the formula (1), wherein $A^2$ is a single bond, a $CH_2$ group or a $CH(CH_3)$ group, and $Cy^1$ is a cyclohexyl group substituted with at least one group selected from the group consisting of a $C_1$-$C_6$ alkoxy group, a $C_1$-$C_6$ haloalkyl group, a $C_1$-$C_3$ alkylthio group, a $C_1$-$C_3$ alkylidene group which forms a double bond with the same carbon atom forming a ring, a hydroxy $C_1$-$C_6$ alkyl group and a $C_2$-$C_4$ alkylcarbonyloxy group;

an amide compound of the formula (1), wherein $Cy^1$ is a $C_3$-$C_6$ cycloalkyl group substituted with at least one group selected from the group consisting of a methoxy group, a trifluoromethyl group, a methylthio group, a $CH_2$ group which forms a double bond with the same carbon atom forming a ring, and a hydroxymethyl group;

an amide compound of the formula (1), wherein $A^2$ is a single bond, a $CH_2$ group or a $CH(CH_3)$ group, and $Cy^1$ is a $C_3$-$C_6$ cycloalkyl group substituted with at least one group selected from the group consisting of a methoxy group, a trifluoromethyl group, a methylthio group, a $CH_2$ group which forms a double bond with the same carbon atom forming a ring, and a hydroxymethyl group;

an amide compound of the formula (1), wherein $A^2$ is a single bond, a $CH_2$ group or a $CH(CH_3)$ group, and $Cy^1$ is a cyclohexyl group substituted with at least one group selected from the group consisting of a methoxy group, a trifluoromethyl group, a methylthio group, a $CH_2$ group which forms a double bond with the same carbon atom forming a ring, and a hydroxymethyl group;

an amide compound of the formula (1), wherein $A^2$ is a single bond, a $CH_2$ group or a $CH(CH_3)$ group, and $Cy^1$ is a $C_3$-$C_6$ cycloalkyl group substituted with a hydroxymethyl group;

an amide compound of the formula (1), wherein $Cy^1$ is a cyclohexyenyl group optionally substituted with at least one group selected from the group [a-1];

an amide compound of the formula (1), wherein $Cy^1$ is a $C_3$-$C_6$ cycloalkenyl group optionally substituted with at least one group selected from the group [b-1];

an amide compound of the formula (1), wherein $Cy^1$ is a cyclohexenyl group optionally substituted with at least one group selected from the group [b-1];

an amide compound of the formula (1), wherein $Cy^1$ is a $C_3$-$C_6$ cycloalkenyl group optionally substituted with at least one group selected from the group consisting of a $C_1$-$C_6$ alkoxy group, a $C_3$-$C_6$ alkenyloxy group, a $C_1$-$C_6$ haloalkyl group, a $C_1$-$C_6$ haloalkoxy group, a $C_1$-$C_3$ alkylthio group, a $C_1$-$C_3$ alkylidene group which forms a double bond with the same carbon atom forming a ring, a hydroxy $C_1$-$C_6$ alkyl group, a $C_2$-$C_4$ alkylcarbonyloxy group, a (di($C_1$-$C_3$ alkyl)amino)$C_1$-$C_6$ alkyl group, a $C_2$-$C_6$ cyanoalkyl group and a phenoxy group;

an amide compound of the formula (1), wherein $Cy^1$ is a $C_3$-$C_6$ cycloalkenyl group;

an amide compound of the formula (1), wherein $Cy^1$ is a cyclohexenyl group;

an amide compound of the formula (1), wherein $Cy^1$ is a 1-cyclohexenyl group;

an amide compound of the formula (1), wherein $Cy^1$ is a cyclohexyl group which is optionally substituted with at least one group selected from the group [a-1] and in which one of methylenes forming the ring is replaced with a carbonyl group;

an amide compound of the formula (1), wherein $Cy^1$ is a $C_3$-$C_6$ cycloalkyl group which is optionally substituted with at least one group selected from the group [b-1] and in which one of methylenes forming the ring is replaced with a carbonyl group;

an amide compound of the formula (1), wherein $Cy^1$ is a cyclohexyl group which is optionally substituted with at least one group selected from the group [b-1] and in which one of methylenes forming the ring is replaced with a carbonyl group;

an amide compound of the formula (1), wherein $Cy^1$ is a $C_3$-$C_6$ cycloalkyl group which is optionally substituted with at least one group selected from the group consisting of a $C_1$-$C_6$ alkoxy group, a $C_3$-$C_6$ alkenyloxy group, a $C_1$-$C_6$ haloalkyl group, a $C_1$-$C_6$ haloalkoxy group, a $C_1$-$C_3$ alkylthio group, a $C_1$-$C_3$ alkylidene group which forms a double bond with the same carbon atom forming a ring, a hydroxy $C_1$-$C_6$ alkyl group, a $C_2$-$C_4$ alkylcarbonyloxy group, a (di($C_1$-$C_3$ alkyl)amino)$C_1$-$C_6$ alkyl group, a $C_2$-$C_6$ cyanoalkyl group and a phenoxy group and in which one of methylenes forming the ring is replaced with a carbonyl group;

an amide compound of the formula (1), wherein $Cy^1$ is a $C_3$-$C_6$ cycloalkyl group in which one of methylenes forming the ring is replaced with a carbonyl group;

an amide compound of the formula (1), wherein $Cy^1$ is a cyclohexyl group in which one of methylenes forming the ring is replaced with a carbonyl group;

an amide compound of the formula (1), wherein $Cy^1$ is a 2-oxocyclohexyl group;

an amide compound of the formula (1), wherein $Cy^1$ is hydroxyiminocyclohexyl group optionally substituted with at least one group selected from the group [a-1];

an amide compound of the formula (1), wherein $Cy^1$ is a $C_3$-$C_6$ hydroxyiminocycloalkyl group optionally substituted with at least one group selected from the group [b-1];

an amide compound of the formula (1), wherein $Cy^1$ is a hydroxyiminocyclohexyl group optionally substituted with at least one group selected from the group [b-1];

an amide compound of the formula (1), wherein $Cy^1$ is a $C_3$-$C_6$ hydroxyiminocycloalkyl group optionally substituted with at least one group selected from the group consisting of a $C_1$-$C_6$ alkoxy group, a $C_3$-$C_6$ alkenyloxy group, a $C_1$-$C_6$ haloalkyl group, a $C_1$-$C_6$ haloalkoxy group, a $C_1$-$C_3$ alkylthio group, a $C_1$-$C_3$ alkylidene group which forms a double bond with the same carbon atom forming a ring, a hydroxy $C_1$-$C_6$ alkyl group, a $C_2$-$C_4$ alkylcarbonyloxy group, a (di($C_1$-$C_3$ alkyl)amino)$C_1$-$C_6$ alkyl group, a $C_2$-$C_6$ cyanoalkyl group and a phenoxy group;

an amide compound of the formula (1), wherein $Cy^1$ is a $C_3$-$C_6$ hydroxyiminocycloalkyl group;

an amide compound of the formula (1), wherein $X^2$ is a hydrogen atom or a halogen atom, and $X^3$ is a halogen atom;

an amide compound of the formula (1), wherein $X^1$ is a fluorine atom, $X^2$ is a hydrogen atom or a halogen atom, and $X^3$ is a halogen atom;

an amide compound of the formula (1), wherein $X^2$ is a hydrogen atom or a halogen atom, $X^3$ is a halogen atom, and A is $A^1$-$CR^{11}R^{12}R^{13}$;

an amide compound of the formula (1), wherein $X^2$ is a hydrogen atom or a halogen atom, $X^3$ is a halogen atom, and A is $A^2$-$Cy^1$;

an amide compound of the formula (1), wherein $X^2$ is a hydrogen atom or a halogen atom, $X^3$ is a halogen atom, A is $A^2$-$Cy^1$, and $A^2$ is a single bond, a $CH_2$ group or a $CH(CH_3)$ group;

an amide compound of the formula (1), wherein $X^1$ is a fluorine atom, $X^2$ is a hydrogen atom or a halogen atom, $X^3$ is a halogen atom, A is $A^2$-$Cy^1$, and $A^2$ is a single bond, a $CH_2$ group or a $CH(CH_3)$ group;

an amide compound of the formula (1), wherein $X^2$ is a hydrogen atom or a halogen atom, $X^3$ is a halogen atom, and A is $A^3$-$Cy^2$;

an amide compound of the formula (1), wherein $X^2$ is a fluorine atom, $X^3$ is a fluorine atom, A is $A^2$-$Cy^1$, and $A^2$ is a single bond, a $CH_2$ group or a $CH(CH_3)$ group;

an amide compound of the formula (1), wherein A is $A^3$-$Cy^2$;

an amide compound of the formula (1), wherein A is $A^3$-$Cy^2$, $A^3$ is a methylene group substituted with a $C_1$-$C_3$ haloalkyl group or a cyano group, and $Cy^2$ is a $C_3$-$C_6$ cycloalkyl group optionally substituted with at least one group selected from the group [a-2];

an amide compound of the formula (1), wherein A is $A^3$-$Cy^2$, $A^3$ is a methylene group substituted with at least one group selected from the group consisting of a $C_1$-$C_3$ haloalkyl group, a $C_2$-$C_4$ alkenyl group, a $C_2$-$C_4$ alkynyl group, a cyano group and a phenyl group, and $Cy^2$ is a $C_3$-$C_6$ cycloalkyl group optionally substituted with at least one group selected from the following group [b-2], wherein the group [b-2] consists of:
a halogen atom, a $C_1$-$C_4$ alkyl group, a $C_2$-$C_4$ alkenyl group, a $C_2$-$C_4$ alkynyl group, a hydroxyl group, a cyano group, a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a $C_1$-$C_3$ alkylidene group which forms a double bond with the same carbon atom forming a ring, a hydroxy $C_1$-$C_6$ alkyl group, a $C_2$-$C_4$ alkylcarbonyloxy group, a (di($C_1$-$C_3$ alkyl)amino)$C_1$-$C_6$ alkyl group, a carbamoyl group, a formyl group, a $C_2$-$C_6$ cyanoalkyl group, a $C_1$-$C_3$ alkylsulfonyl group and a phenoxy group;

an amide compound of the formula (1), wherein A is $A^3$-$Cy^2$, $A^3$ is a methylene group substituted with at least one group selected from the group consisting of a $C_1$-$C_3$ haloalkyl group, a $C_2$-$C_4$ alkenyl group, a $C_2$-$C_4$ alkynyl group, a cyano group and a phenyl group, and $Cy^2$ is a cyclohexyl group optionally substituted with at least one group selected from the above group [b-2];

an amide compound of the formula (1), wherein A is $A^3$-$Cy^2$, and $A^3$ is a methylene group substituted with at least one group selected from the group consisting of a $C_1$-$C_3$ haloalkyl group, a $C_2$-$C_4$ alkenyl group and a $C_2$-$C_4$ alkynyl group:

an amide compound of the formula (1), wherein A is $A^3$-$Cy^2$, $A^3$ is a methylene group substituted with a $C_1$-$C_3$ haloalkyl group and a cyano group, $Cy^2$ is a $C_3$-$C_6$ cycloalkyl group optionally substituted with at least one group selected from the above group [b-2];

an amide compound of the formula (1), wherein A is $A^3$-$Cy^2$, $A^3$ is a methylene group substituted with a $C_1$-$C_3$ haloalkyl group and a cyano group, and $Cy^2$ is a cyclohexyl group optionally substituted with at least one group selected from the above group [b-2];

an amide compound of the formula (1), wherein A is $A^3$-$Cy^2$, $A^3$ is a methylene group substituted with a $C_1$-$C_3$ haloalkyl group or a cyano group, and $Cy^2$ is a $C_3$-$C_6$ cycloalkyl group optionally substituted with a $C_1$-$C_4$ alkyl group;

an amide compound of the formula (1), wherein A is $A^3$-$Cy^2$, $A^3$ is a methylene group substituted with a $C_1$-$C_3$ haloalkyl group or a cyano group, and $Cy^2$ is a cyclohexyl group optionally substituted with a $C_1$-$C_4$ alkyl group;

an amide compound of the formula (1), wherein A is $A^3$-$Cy^2$, $A^3$ is a methylene group substituted with a $C_1$-$C_3$ haloalkyl group or a cyano group, and $Cy^2$ is a cyclopentyl group optionally substituted with a $C_1$-$C_4$ alkyl group; and an amide compound of the formula (1), wherein A is $A^3$-$Cy^2$, $A^3$ is a methylene group substituted with a $C_1$-$C_3$ haloalkyl group or a cyano group, and $Cy^2$ is a cyclobutyl group optionally substituted with a $C_1$-$C_4$ alkyl-group.

In the specification, a structural formula of a compound may conveniently represent a specific isomer. However, the present invention includes all active isomers such as geometrical isomers, optical isomers, steric isomers and tautomers which may be generated due to the structure of a compound, and a mixture of isomers. In the present invention, a compound is not limited to the description of a specific formula conveniently described and may be any one of isomers or a mixture of isomers. Therefore, in the present invention, a compound may have an asymmetric carbon atom in its molecule and thus may exist as an optically active form or a racemate. In the present invention, there is no limitation, and all cases are included.

Then, a process for producing the compound of the present invention is explained.

The compound of the present invention can be produced, for example, by the following Production process 1 to Production process 9.

(Production Process 1)

Of compounds of the present invention, a compound (5) of the present invention in which Z is an oxygen atom can be produced by reacting a compound (2) and a compound (3) in the presence of a dehydration condensing agent.

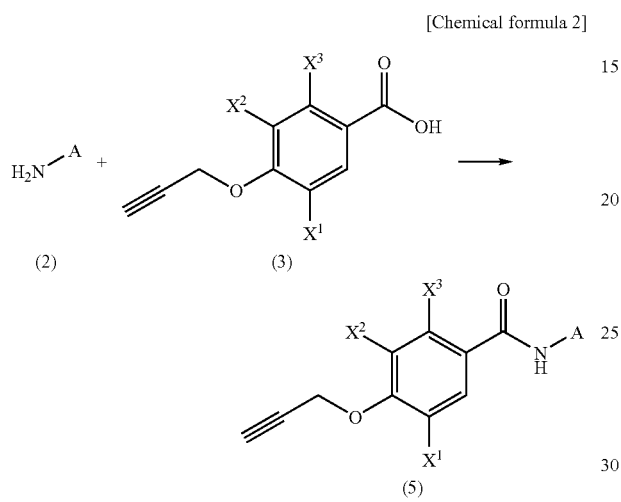

[Chemical formula 2]

In the formulae, A, $X^1$, $X^2$ and $X^3$ are as defined above.

The reaction is usually performed in the presence of a solvent.

Examples of the solvent used in the reaction include ethers such as tetrahydrofuran (hereinafter, referred to as THF in some cases), ethylene glycol dimethyl ether and tert-butyl methyl ether (hereinafter, referred to as MTBE in some cases), aliphatic hydrocarbons such as hexane, heptane and octane, aromatic hydrocarbons such as toluene and xylene, halogenated hydrocarbons such as chlorobenzene, esters such as butyl acetate and ethyl acetate, nitrites such as acetonitrile, acid amides such as N,N-dimethylformamide (hereinafter, referred to as DMF in some cases), sulfoxides such as dimethyl sulfoxide (hereinafter, referred to as DMSO in some cases), and a mixture thereof.

Examples of the dehydration condensing agent used in the reaction include carbodiimides such as 1-ethyl-3-(3-dimethylaminopropyl)carbodiimide hydrochloride (hereinafter, referred to as WSC) and 1,3-dicyclohexylcarbodiimide.

The used amount of the compound (3) is usually 1 to 3 mol per 1 mol of the compound (2). The used amount of the dehydration condensing agent is usually 1 to 5 mol per 1 mol of the compound (2).

The reaction temperature is usually in a range of from 0 to 140° C., and the reaction time is usually in a range of from 1 to 24 hours.

After completion of the reaction, the compound (5) of the present invention can be isolated by post-treatment such as filtration of the reaction mixture, extraction of the filtrate with an organic solvent, and drying and concentration of an organic layer.

The isolated compound (5) of the present invention can be further purified by chromatography, recrystallization or the like.

(Production Process 2)

Of compounds of the present invention, a compound (5) of the present invention in which Z is an oxygen atom can be produced by reacting a compound (2) and a compound (4) in the presence of a base.

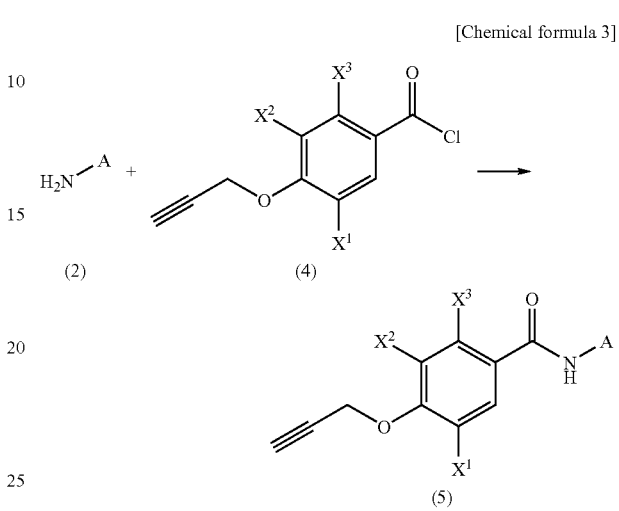

[Chemical formula 3]

In the formulae, A, $X^1$, $X^2$ and $X^3$ are as defined above.

The reaction is usually performed in the presence of a solvent.

Examples of the solvent used in the reaction include ethers such as THF, ethylene glycol dimethyl ether and MTBE, aliphatic hydrocarbons such as hexane, heptane and octane, aromatic hydrocarbons such as toluene and xylene, halogenated hydrocarbons such as chlorobenzene, esters such as butyl acetate and ethyl acetate, nitrites such as acetonitriles, acid amides such as DMF, sulfoxides such as DMSO, and a mixture thereof.

Examples of the base used in the reaction include alkali metal carbonates such as sodium carbonate and potassium carbonate, tertiary amines such as triethyl amine and diisopropylethylamine, and nitrogen-containing aromatic compounds such as pyridine and 4-dimethylaminopyridine.

The used amount of the compound (4) is usually 1 to 3 mol per 1 mol of the compound (2). The used amount of the base is usually 1 to 10 mop per 1 mol of the compound (2).

The reaction temperature is usually in a range of from −20 to 100° C., and the reaction time is usually in a range of from 0.1 to 24 hours.

After completion of the reaction, the compound (5) of the present invention can be isolated by post-treatment such as filtration of the reaction mixture, extraction of the filtrate with an organic solvent, and drying and concentration of an organic layer.

The isolated compound (5) of the present invention can be further purified by chromatography, recrystallization or the like.

(Production Process 3)

Of compounds of the present invention, a compound (6) of the present invention in which Z is a sulfur atom can be produced by reacting the compound (5) of the present invention in which Z is an oxygen atom and 2,4-bis(4-methoxyphenyl)-1,3-dithia-2,4-diphosphethane-2,4-disulfide (hereinafter, referred to as Lawesson's reagent).

[Chemical formula 4]

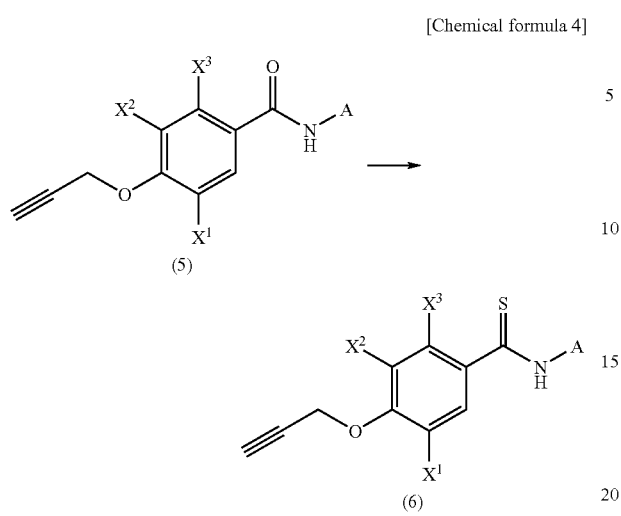

In the formulae, A, $X^1$, $X^2$ and $X^3$ are as define above.

The reaction is usually performed in the presence of a solvent.

Examples of the solvent used in the reaction include ethers such as THF, ethylene glycol dimethyl ether and MTBE, aliphatic hydrocarbons such as hexane, heptane and octane, aromatic hydrocarbons such as toluene and xylene, halogenated hydrocarbons such as chlorobenzene, organic nitriles such as acetonitrile and butyronitrile, sulfoxides such as dimethyl sulfoxide, and a mixture thereof.

The used amount of the Lawessen's reagent is usually 1 to 2 mol per 1 mol of the compound (5) of the present invention.

The reaction temperature is usually in a range of from 25 to 150° C., and the reaction time is a usually in a range of from 0.1 to 24 hours.

After completion of the reaction, the compound (6) of the present invention can be isolated by post-treatment such as extraction of the reaction mixture with an organic solvent, and drying and concentration of an organic layer. The isolated compound (6) of the present invention can be further purified by chromatography, recrystallization or the like.

(Production Process 4)

Of compounds of the present invention, a compound (9) of the present invention in which Z is an oxygen atom and $X^1$ is a fluorine atom can be produced by reacting a compound (7) and a compound (2) in the presence of a base to obtain a compound (8) (step (IV-1)) and then reacting the compound (8) and propargyl alcohol in the presence of a base (step (IV-2)).

[Chemical formula 5]

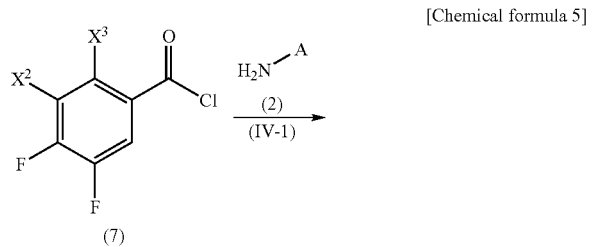

In the formulae, A, $X^2$ and $X^3$ are as defined above.

Step (IV-1)

The reaction is usually performed in the presence of a solvent.

Examples of the solvent used in the reaction include ethers such as THF, ethylene glycol dimethyl ether and MTBE, aliphatic hydrocarbons such as hexane, heptane and octane, aromatic hydrocarbons such as toluene and xylene, halogenated hydrocarbons such as chlorobenzene, esters such as butyl acetate and ethyl acetate, nitrites such as acetonitrile, acid amides such as DMF, sulfoxides such as dimethyl sulfoxide, and a mixture thereof.

Examples of the base used in the reaction include alkali metal carbonates such as sodium carbonate and potassium carbonate, tertiary amines such as triethylamine and diisopropylethylamine, and nitrogen-containing aromatic compounds such as pyridine and 4-dimethylaminopyridine.

The used amount of the compound (7) is usually 1 to 3 mol per 1 mol of the compound (2). The used amount of the base usually 1 to 10 mol per 1 mol of the compound (2).

The reaction temperature is usually in a range of from −20 to 100° C., and the reaction time is usually in a range of from 0.1 to 24 hours.

After completion of the reaction, the compound (8) can be isolated by post-treatment such as extraction of the reaction mixture with an organic solvent, and drying and concentration of an organic layer. The isolated compound (8) can be further purified by chromatography, recrystallization or the like.

Step (IV-2)

The reaction is usually performed in the presence of a solvent.

Examples of the solvent used in the reaction include ethers such as THF, ethylene glycol dimethyl ether and MTBE, aliphatic hydrocarbons such as hexane, heptane and octane, ketones such as acetone, methyl ethyl ketone and methyl isobutyl ketone, aromatic hydrocarbons such as toluene and xylene, halogenated hydrocarbons such as chlorobenzene, esters such as butyl acetate and ethyl acetate, nitrites such as acetonitrile, acid amides such as DMF, sulfoxides such as dimethyl sulfoxide, and a mixture thereof.

Examples of the base used in the reaction include alkali metal carbonates such as sodium carbonate and potassium carbonate, alkali metal hydrogen carbonates such as sodium hydrogen carbonate, alkali metal hydrides such as sodium hydride, and alkali metal hydroxides such as sodium hydroxide.

The used amount of propargyl alcohol is usually 1 to 3 mol per 1 mol of the compound (8). The used amount of the base is usually 1 to 2 mol per 1 mol of the compound (8).

The reaction temperature is usually in a range of from −20 to 100° C., and the reaction time is usually in a range of from 0.1 to 24 hours.

After completion of the reaction, the compound (9) of the present invention can be isolated by post-treatment such as extraction of the reaction mixture with an organic solvent, and drying and concentration of an organic layer. The isolated compound (9) of the present invention can be further purified by chromatography, recrystallization or the like.

(Production Process 5)

Of compounds of the present invention, a compound (5) of the present invention in which Z is an oxygen atom can be produced by reacting a compound (10) and propargyl bromide in the presence of a base.

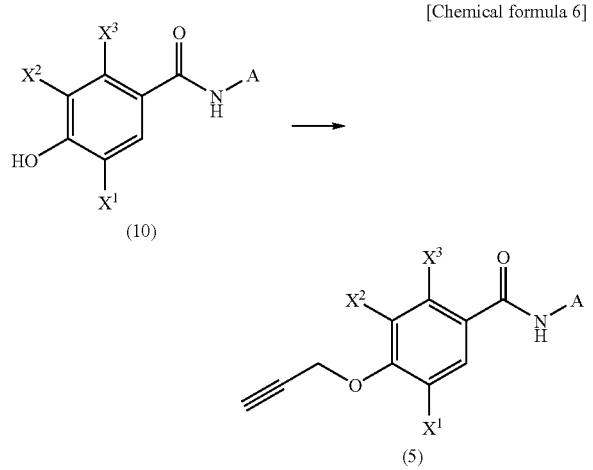

In the formulae, A, $X^1$, $X^2$ and $X^3$ are as defined above.

The reaction is usually performed in the presence of a solvent.

Examples of the solvent used in the reaction include ethers such as THF, ethylene glycol dimethyl ether and MTBE, aromatic hydrocarbons such as toluene and xylene, halogenated hydrocarbons such as chlorobenzene, nitriles such as acetonitrile, acid amides such as DMF, sulfoxides such as dimethyl sulfoxide, ketones such as acetone, methyl ethyl ketone and methyl isobutyl ketone, water, and a mixture thereof.

Examples of the base used in the reaction include alkali metal carbonates such as sodium carbonate, potassium carbonate and cesium carbonate, alkali metal hydroxides such as sodium hydroxide, and alkali metal hydrides such as sodium hydride.

The used amount of propargyl bromide is usually 1 to 3 mol per 1 mol of the compound (10). The used amount of the base is usually 1 to 3 mol per 1 mol of the compound (10).

The reaction temperature is usually in a range of from −20 to 100° C., and the reaction time is usually in a range of from 0.1 to 24 hours.

After completion of the reaction, the compound (5) of the present invention can be isolated by post-treatment such as extraction of the reaction mixture with an organic solvent, and drying and concentration of an organic layer. The isolated compound (5) of the present invention can be further purified by chromatography, recrystallization or the like.

(Production Process 6)

Of compounds of the present invention, a compound (13) of the present invention in which Z is an oxygen atom, A is $A^2$-$Cy^1$, $A^2$ is a single bond and $Cy^1$ is a 2-($C_1$-$C_3$ alkylthio)cyclohexyl group, a 2-($C_1$-$C_6$ alkoxy)cyclohexyl group or a 2-phenoxycyclohexyl group can be produced by a process shown in the following scheme.

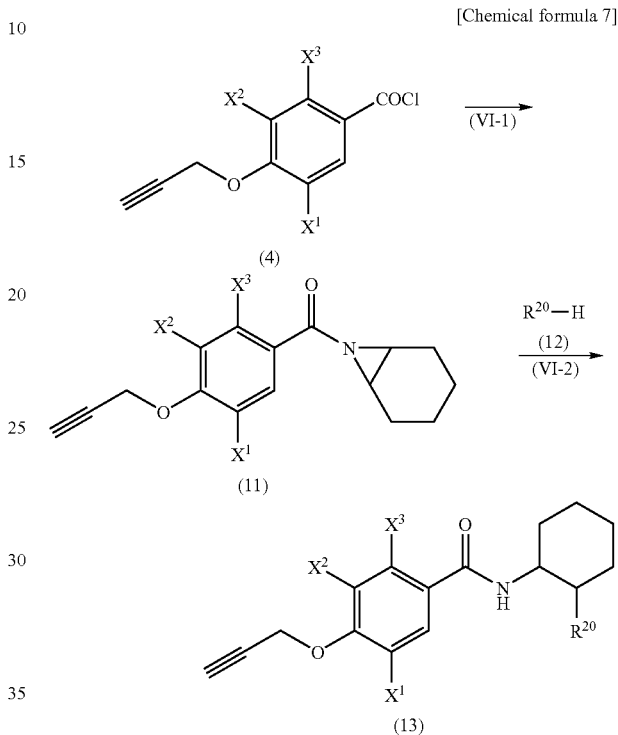

In the formulae, $X^1$, $X^2$ and $X^3$ are as defined above, and $R^{20}$ represents a $C_1$-$C_3$ alkylthio group, a $C_1$-$C_6$ alkoxy group or a phenoxy group.

Step (VI-1)

The compound (11) can be produced by reacting the compound (4) and 7-azabicyclo[4.1.0]heptane in the presence of a base according to the process described in Production process 2.

Step (VI-2)

The compound (13) of the present invention can be produced by reacting the compound (11) and the compound (12).

The reaction is usually performed in the presence of a solvent.

Examples of the solvent used in the reaction include ethers such as THF, ethylene glycol dimethyl ether, and MTBE, aromatic hydrocarbons such as toluene and xylene, halogenated hydrocarbons such as chlorobenzene and chloroform, esters such as butyl acetate and ethyl acetate, nitriles such as acetonitrile, acid amides such as DMF, and a mixture thereof.

The used amount of the compound (12) is usually 1 to 10 mol per 1 mol of the compound (11).

The reaction temperature is usually in a range of from −20 to 150° C., and the reaction time is usually in a range of from 0.1 to 24 hours.

The reaction can be also performed in the presence of an additive, if necessary. Examples of such an additive include a phosphorus compound such as tributylphosphine.

The compound of the formula (12) can be also used in the reaction after a reaction with an alkali metal hydride such as sodium hydride to prepare an alkali metal salt.

After completion of the reaction, the compound (13) of the present invention can be isolated by post-treatment such as extraction of the reaction mixture with an organic solvent, and drying and concentration of an organic layer. The isolated compound (13) of the present invention can be further purified by chromatography, recrystallization or the like.

(Production Process 7)

Of compounds of the present invention, a compound (16) of the present invention in which Z is an oxygen atom, A is $A^2$-$Cy^1$ and $Cy^1$ is a $C_3$-$C_6$ cycloalkyl group which is optionally substituted with at least one group selected from the group [a-1] and in which one of methylenes forming the ring is replaced with a carbonyl group, or A is $A^3$-$Cy^2$ and $Cy^2$ is a $C_3$-$C_6$ cycloalkyl group which is optionally substituted with at least one group selected from the group [a-2] and in which one of methylenes forming the ring is replaced with a carbonyl group can be produced by a process shown in the following scheme.

[Chemical formula 8]

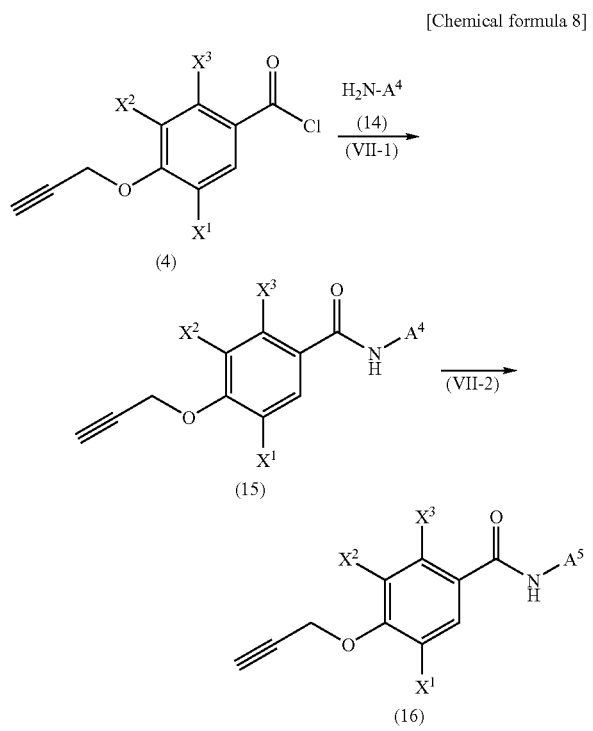

In the formulae, $A^4$ represents $A^2$-$Cy^{11}$ or $A^3$-$Cy^{21}$, $A^5$ represents $A^2$-$Cy^{12}$ or $A^3$-$Cy^{22}$, $Cy^{11}$ represents a $C_3$-$C_6$ cycloalkyl group which is optionally substituted with at least one group selected from the group [a-1] and in which one of methylenes forming the ring is replaced with CH(OH), $Cy^{21}$ represents a $C_3$-$C_6$ cycloalkyl group which is optionally substituted with at least one group selected from the group [a-2] and in which one of methylenes forming the ring is replaced with CH(OH), $Cy^{12}$ represents a $C_3$-$C_6$ cycloalkyl group which is optionally substituted with at least one group selected from the group [a-1] and in which one of methylenes forming the ring is replaced with a carbonyl group, $Cy^{22}$ represents a $C_3$-$C_6$ cycloalkyl group which is optionally substituted with at least one group selected from the group [a-2] and in which one of methylenes forming the ring is replaced with a carbonyl group, and $X^1$, $X^2$, $X^3$, $A^2$ and $A^3$ are as defined above.

Step (VII-1)

The compound (15) can be produced by reacting the compound (4) and the compound (14) in the presence of a base according to the process described in Production process 2.

Step (VII-2)

The compound (16) of the present invention can be produced by reacting the compound (15) and an oxidizing agent.

The reaction is usually performed in the presence of a solvent.

Examples of the solvent used in the reaction include ketones such as acetone, methyl ethyl ketone, and methyl isobutyl ketone, halogenated hydrocarbons such as chloroform, water, and a mixture thereof.

Examples of the oxidizing agent used in the reaction include hypervalent iodine compounds such as bis(acetoxy) phenyl iodide, chromium compounds such as potassium bichromate and chromic acid, halogen oxide compounds such as periodic acid, manganese oxides such as manganese dioxide and potassium permanganate.

The used amount of the oxidizing agent is usually 1 to 10 mol per 1 mol of the compound (15) of the present invention.

The reaction temperature is usually in a range of from −78 to 150° C., and the reaction time is usually in a range of from 0.1 to 24 hours.

After completion of the reaction, the compound (16) of the present invention can be isolated by post-treatment such as pouring of the reaction mixture into water, extraction with an organic solvent, and drying and concentration of an organic layer. The isolated compound (16) of the present invention can be further purified by chromatography, recrystallization or the like.

(Production Process 8)

Of compounds of the present invention, a compound (19) in which Z is an oxygen atom, A is $A^2$-$Cy^1$ and $Cy^1$ is a $C_3$-$C_6$ cycloalkyl group substituted with a $C_1$-$C_3$ alkylidene group which forms a double bond with the same carbon atom forming a ring, or A is $A^3$-$Cy^2$ and $Cy^2$ is a $C_3$-$C_6$ cycloalkyl group substituted with a $C_1$-$C_3$ alkylidene group which forms a double bond with the same carbon atom forming a ring can be produced by reacting a compound (17) and a compound (18) in the presence of a base.

[Chemical formula 9]

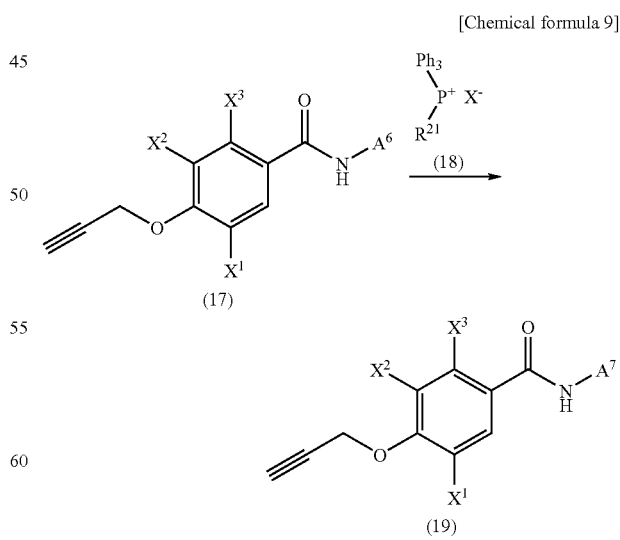

In the formulae, $A^6$ represents $A^2$-$Cy^{13}$ or $A^3$-$Cy^{23}$, $Cy^{13}$ represents a $C_3$-$C_6$ cycloalkyl group in which one of methylenes forming the ring is replaced with a carbonyl group, $Cy^{23}$ represents a $C_3$-$C_6$ cycloalkyl group in which one of methylenes forming the ring is replaced with a carbonyl group, $A^7$ represents $A^2$-$Cy^{14}$ or $A^3$-$Cy^{24}$, $Cy^{14}$ represents a $C_3$-$C_6$ cycloalkyl group substituted with a $C_1$-$C_3$ alkylidene group which forms a double bond with the same carbon atom forming a ring, $Cy^{24}$ represents a $C_3$-$C_6$ cycloalkyl group substituted with a $C_1$-$C_3$ alkylidene group which forms a double bond with the same carbon atom forming a ring, $R^{21}$ represents a $C_1$-$C_3$ alkyl group, X represents a chlorine atom, a bromine atom or an iodine atom, and $X^1$, $X^2$, $X^3$, $A^2$ and $A^3$ are as defined above.

The reaction is usually performed in the presence of a solvent.

Examples of the solvent used in the reaction include ketones such as acetone, methyl ethyl ketone and methyl isobutyl ketone, halogenated hydrocarbons such as chloroform, water, and a mixture thereof.

Examples of the base used in the reaction include alkali metal salts such as tert-butoxy potassium and n-butyl lithium, and alkali metal hydroxides such as sodium hydroxide.

The used amount of the compound of the formula (18) is usually 1 to 10 mol per 1 mol of the compound (17) of the present invention. The used amount of the base is usually 1 to 10 mol per 1 mol of the compound (17) of the present invention.

The reaction temperature is usually in a range of from −78 to 150° C., and the reaction time is usually in a range of from 0.1 to 24 hours.

After completion of the reaction, the compound (19) of the present invention can be isolated by post-treatment such as extraction of the reaction mixture with an organic solvent, and drying and concentration of an organic layer. The isolated compound (19) of the present invention can be further purified by chromatography, recrystallization or the like.
(Production Process 9)

Of compounds of the present invention, a compound (20) of the present invention in which Z is an oxygen atom, and A is $A^2$-$Cy^1$ and $Cy^1$ is a $C_3$-$C_6$ hydroxyiminocycloalkyl group optionally substituted with at least one group selected from the group [a-1], or A is $A^3$-$Cy^2$ and $Cy^2$ is a $C_3$-$C_6$ hydroxyiminocycloalkyl group optionally substituted with at least one group selected from the group [a-2] can be produced by reacting the compound (16) and hydroxylamine or a salt thereof.

In the formulae, $A^8$ represents $A^2$-$Cy^{15}$ or $A^3$-$Cy^{25}$, $Cy^{15}$ represents a $C_3$-$C_6$ hydroxyiminocycloalkyl group optionally substituted with at least one group selected from the group [a-1], $Cy^{25}$ represents a $C_3$-$C_6$ hydroxyiminocycloalkyl group optionally substituted with at least one group selected from the group [a-2], and $A^2$, $A^3$, $A^5$, $X^1$, $X^2$ and $X^3$ are as defined above.

The reaction is usually performed in the presence of a solvent.

Examples of the solvent used in the reaction include ethers such as 1,4-dioxane, tetrahydrofuran and MTBE, aliphatic hydrocarbons such as hexane and heptane, aromatic hydrocarbons such as toluene and xylene, halogenated hydrocarbons such as chlorobenzene, esters such as ethyl acetate, nitrites such as acetonitrile and butyronitrile, acid amides such as DMF, sulfoxides such as dimethyl sulfoxide, alcohols such as methanol and ethanol, water, and a mixture thereof.

The used amount of hydroxylamine or a salt thereof is usually 1 to 5 mol per 1 mol of the compound (16).

The reaction temperature is usually in a range of from 0 to 150° C., and the reaction time is usually in a range of from 0.1 to 24 hours.

After completion of the reaction, the compound (20) of the present invention can be isolated by post-treatment such as extraction of the reaction mixture with an organic solvent, and drying and concentration of an organic layer. The isolated compound (20) of the present invention can be further purified by chromatography, recrystallization of the like.

A part of intermediates used for production of the compound of the present invention are commercially available or disclosed in known literatures. Such intermediates can be produced, for example, by the following processes.
(Intermediate Production Process 1)

The compound (3) and the compound (4) can be produced by the process shown in the following scheme.

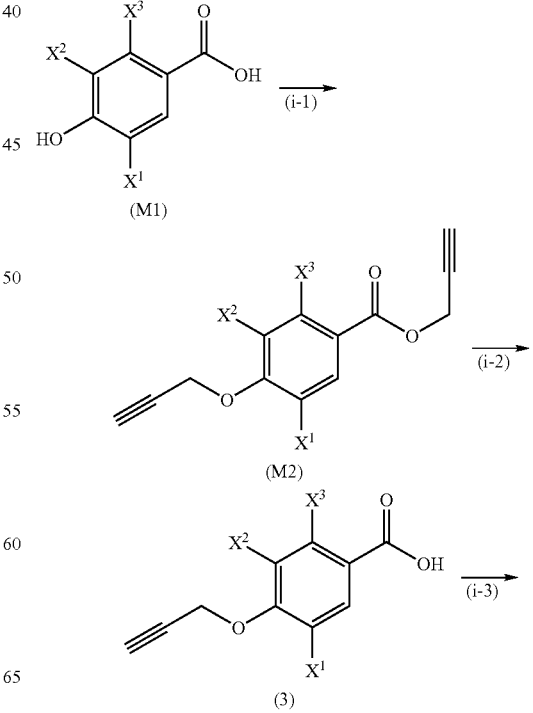

[Chemical formula 11]

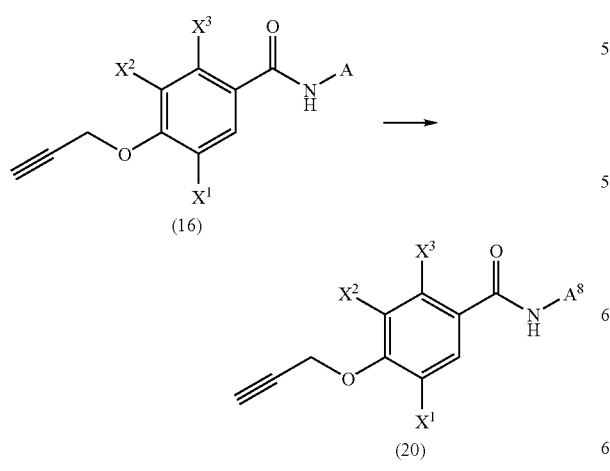

[Chemical formula 10]

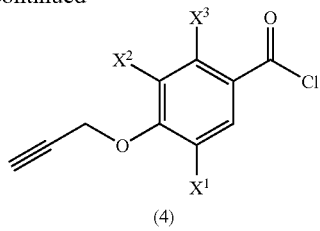

(4)

In the formulae, $X^1$, $X^2$ and $X^3$ are as defined above.

Step (i-1)

The compound (M2) can be produced by reacting the compound (M1) and propargyl bromide in the presence of a base.

The reaction is usually performed in the presence of a solvent.

Examples of the solvent used in the reaction include acid amides such as DMF and sulfoxides such as DMSO.

Examples of the base used in the reaction include alkali metal carbonates such as sodium carbonate, potassium carbonate and cesium carbonate, and alkali metal hydroxides such as sodium hydroxide.

The used amount of propargyl bromide is usually 2 to 5 mol per 1 mol of the compound (M1). The amount used of the base is usually 2 to 5 mol per 1 mol of the compound (M1).

The reaction temperature is usually in a range of from 0 to 140° C., and the reaction time is usually in a range of from 0.5 to 24 hours.

After completion of the reaction, the compound (M2) can be isolated by post-treatment such as extraction of the reaction mixture with an organic solvent, and drying and concentration of an organic layer. The isolated compound (M2) can be further purified by chromatography, recrystallization or the like.

Step (i-2)

The compound (3) can be produced by hydrolyzing the compound (M2) in the presence of a base.

The reaction is usually performed in the presence of a solvent.

Examples of the base used in the reaction include alkali metal hydroxides such as sodium hydroxide and potassium hydroxide.

Examples of the solvent used in the reaction include ethers such as tetrahydrofuran, ethylene glycol dimethyl ether and tert-butyl methyl ether, alcohols such as methanol and ethanol, water, and a mixture thereof.

The used amount of the base is usually 1 to 10 mol per 1 mol of the compound (M2).

The reaction temperature is usually in a range of from 0 to 120° C., and the reaction time is usually in a range of from 0.5 to 24 hours.

After completion of the reaction, the reaction solution is made acidic. In the case where a solid is precipitated, the compound (3) can be isolated by filtration. In the case where a solid is not precipitated, the compound (3) can be isolated by post-treatment such as extraction of the reaction mixture with an organic solvent, and drying and concentration of an organic layer. The isolated compound (3) can be further purified by chromatography, recrystallization or the like.

Step (i-3)

The compound (4) can be produced by reacting the compound (3) and thionyl chloride.

The reaction is usually performed in the presence of a solvent.

Examples of the solvent used in the reaction include aliphatic hydrocarbons such as hexane, heptane and octane, aromatic hydrocarbons such as toluene and xylene, nitriles such as acetonitrile, halogenated hydrocarbons such as chlorobenzene, acid amides such as DMF, and a mixture thereof.

The used amount of thionyl chloride is usually 1 to 2 mol per 1 mol of the compound (3).

The reaction temperature is usually in a range of from 20 to 120° C., and the reaction time is usually in a range of from 0.1 to 24 hours.

After completion of the reaction, the compound (4) can be isolated by post-treatment such as concentration of the reaction mixture. The isolated compound (4) can be further purified by chromatography, recrystallization or the like.

(Intermediate Production Process 2)

The compound (10) can be produced by the process shown in the following scheme.

[Chemical formula 12]

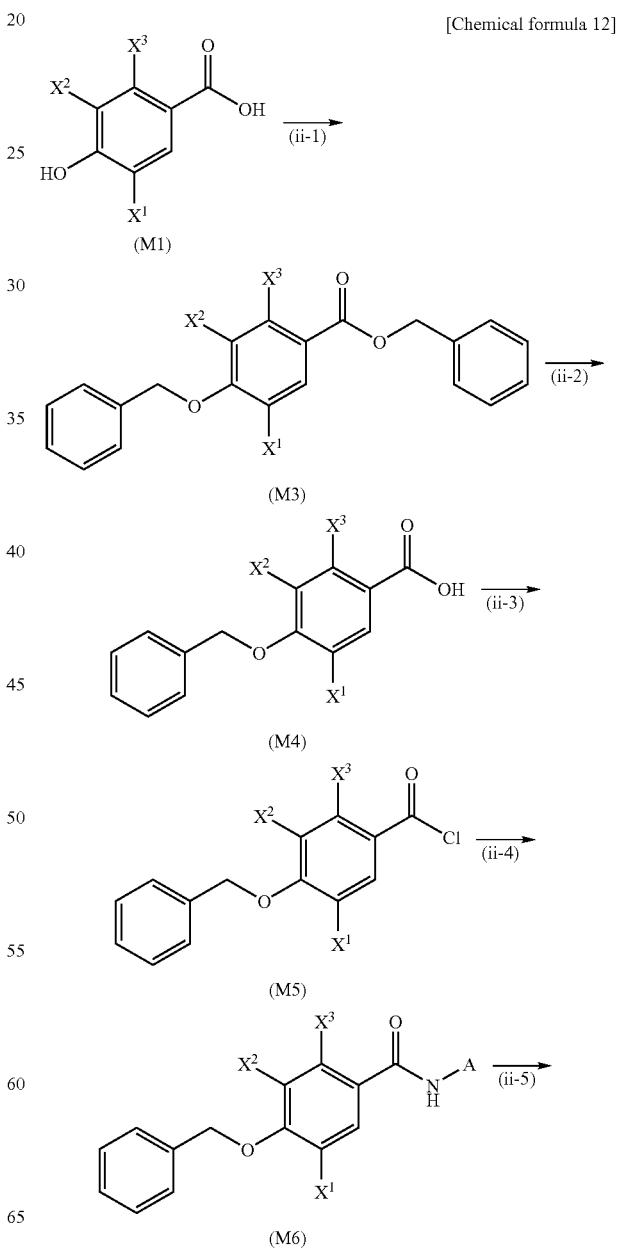

(10)

[Structure: benzamide with X³ and C(=O)NH-A at positions 1,2; X² at 3; HO at 4; X¹ at 5]

In the formulae, A, $X^1$, $X^2$ and $X^3$ are as defined above.

Step (ii-1)

The compound (M3) can be produced by reacting the compound (M1) and benzyl bromide in the presence of a base.

The reaction is usually performed in the presence of a solvent.

Examples of the solvent used in the reaction include acid amides such as DMF, and sulfoxides such as DMSO.

Examples of the base used in the reaction include alkali metal carbonates such as sodium carbonate, potassium carbonate and cesium carbonate, and alkali metal hydroxides such as sodium hydroxide.

The used amount of benzyl bromide is usually 2 to 5 mol per 1 mol of the compound (M1). The used amount of the base is usually 2 to 5 mol per 1 mol of the compound (M1).

The reaction temperature is usually in a range of from 0 to 140° C., and the reaction time is usually in a range of from 0.5 to 24 hours.

After completion of the reaction, the compound (M3) can be isolated by post-treatment such as extraction of the reaction mixture with an organic solvent, and drying and concentration of an organic layer. The isolated compound (M3) can be further purified by chromatography, recrystallization or the like.

Step (ii-2)

The compound (M4) can be produced by hydrolyzing the compound (M3) in the presence of a base.

The reaction is usually performed in the presence of a solvent.

Examples of the base used in the reaction include alkali metal hydroxides such as sodium hydroxide and potassium hydroxide.

Examples of the solvent used in the reaction include ethers such as tetrahydrofuran, ethylene glycol dimethyl ether and MTBE, alcohols such as methanol and ethanol, water, and a mixture thereof.

The used amount of the base is usually 1 to 10 mol per 1 mol of the compound (M3).

The reaction temperature is usually in a range of from 0 to 120° C., and the reaction time is usually in a range of from 0.5 to 24 hours.

After completion of the reaction, the reaction solution is made acidic. In the case where a solid is precipitated, the compound (M4) can be isolated by filtration. In the case where a solid is not precipitated, the compound (M4) can be isolated by post-treatment such as extraction of the reaction mixture with an organic solvent, and drying and concentration of an organic layer. The isolated compound (M4) can be further purified by chromatography, recrystallization of the like.

Step (ii-3)

The compound (M5) can be produced by reacting the compound (M4) and thionyl chloride.

The reaction is usually performed in the presence of a solvent.

Examples of the solvent used in the reaction include aliphatic hydrocarbons such as hexane, heptane and octane, aromatic hydrocarbons such as toluene and xylene, nitriles such as acetonitrile, halogenated hydrocarbons such as chlorobenzene, acid amides such as DMF, and a mixture thereof.

The used amount of thionyl chloride is usually 1 to 2 mol per 1 mol of the compound (M4).

The reaction temperature is usually in a range of from 20 to 120° C., and the reaction time is usually in a range of from 0.1 to 24 hours.

After completion of the reaction, the compound (M5) can be isolated by post-treatment such as concentration of the reaction mixture. The isolated compound (M5) can be further purified by chromatography, recrystallization or the like.

Step (ii-4)

The compound (M6) can be produced by reacting the compound (M5) and the compound (2) in the presence of a base according to the process described in Production process 2.

Step (ii-5)

The compound (10) can be produced by reacting the compound (M6) with hydrogen in the presence of palladium carbon.

The reaction is usually performed in the presence of a solvent.

Examples of the solvent used in the reaction include aliphatic hydrocarbons such as hexane, heptane and octane, aromatic hydrocarbons such as toluene and xylene, alcohols such as methanol and ethanol, esters such as ethyl acetate, ethers such as THF and MTBE, water, and a mixture thereof.

The used amount of palladium carbon is 0.01 to 0.1 mol per 1 mol of the compound (M6). The used amount of hydrogen is usually 1 to 2 mol per 1 mol of the compound (M6).

The reaction temperature is usually in a range of from 0 to 50° C., and the reaction time is usually in a range of from 0.1 to 24 hours.

The pressure of hydrogen used in the reaction is in a range of normal pressure to 10 atoms.

After completion of the reaction, the compound (10) can be isolated by post-treatment such as filtration and concentration of the reaction mixture. The isolated compound (10) can be further purified by chromatography, recrystallization or the like.

Examples of a compound represented by the formula (3):

[Chemical formula 13]

[Chemical formula 13]

(3)

[Structure: benzoic acid with X³, C(=O)OH, X², propargyloxy (HC≡C-CH₂-O-), X¹ substituents]

wherein $X^1$, $X^2$ and $X^3$ are as defined above, which is an intermediate for producing the compound of the present invention include the following compounds:

a compound of the formula (3), wherein $X^1$ is a fluorine atom;

a compound of the formula (3), wherein $X^1$ is a methoxy group;

a compound of the formula (3), wherein $X^2$ is a hydrogen atom;

a compound of the formula (3), wherein $X^3$ is a fluorine atom;

a compound of the formula (3), wherein $X^1$ and $X^3$ are each a fluorine atom;

a compound of the formula (3), wherein $X^1$ is a methoxy group and $X^3$ is a fluorine atom; and a compound of the formula (3), wherein $X^2$ is a hydrogen atom and $X^3$ is a fluorine atom.

Examples of a compound represented by the formula (10):

[Chemical formula 14]

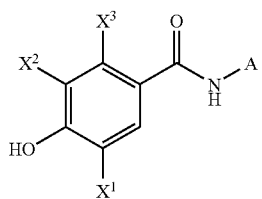

(10)

wherein $X^1$, $X^2$, $X^3$, and A are as defined above, which is an intermediate for producing the compound of the present invention include the following compounds:

a compound of the formula (10), wherein $X^1$ is a fluorine atom;

a compound of the formula (10), wherein $X^1$ is a methoxy group;

a compound of the formula (10), wherein $X^2$ is a hydrogen atom;

a compound of the formula (10), wherein $X^3$ is a fluorine atom;

a compound of the formula (10), wherein $X^1$ and $X^3$ are each a fluorine atom;

a compound of the formula (10), wherein $X^1$ is a methoxy group and $X^3$ is a fluorine atom; and a compound of the formula (10), wherein $X^2$ is a hydrogen atom and $X^3$ is a fluorine atom.

Examples of a compound represented by the formula (11):

[Chemical formula 15]

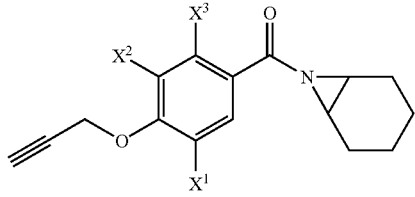

(11)

wherein $X^1$, $X^2$ and $X^3$ are as defined above, which is an intermediate for producing the compound of the present invention include the following compounds:

a compound of the formula (11), wherein $X^1$ is a fluorine atom;

a compound of the formula (11), wherein $X^1$ is a methoxy group;

a compound of the formula (11), wherein $X^2$ is a hydrogen atom;

a compound of the formula (11), wherein $X^3$ is a fluorine atom;

a compound of the formula (11), wherein $X^1$ and $X^3$ are each a fluorine atom;

a compound of the formula (11), wherein $X^1$ is a methoxy group and $X^3$ is a fluorine atom; and a compound of the formula (11), wherein $X^2$ is a hydrogen atom and $X^3$ is a fluorine atom.

Plant diseases against which the compound of the present invention exerts an excellent effect include those caused by fungi, bacteria and viruses. Specific examples of the fungi include genus *Erysiphe* such as wheat powdery mildew (*Erysiphe graminis*), genus *Uncinula* such as grape powdery mildew (*Uncinula necator*), genus *Podosphaera* such as apple powdery mildew (*Podosphaera leucotricha*), genus *Sphaerotheca* such as cucumber powdery mildew (*Sphaerotheca cucurbitae*), genus *Oidiopsis* such as tomato powdery mildew (*Oidiopsis sicula*), genus *Magnaporthe* such as rice blast (*Magnaporthe oryzae*), genus *Cochliobolus* such as rice brown spot (*Cochliobolus miyabeanus*), genus *Mycosphaerella* such as wheat leaf blotch (*Mycosphaerella graminicola*), genus *Pyrenophora* such as barley net blotch (*Pyrenophora teres*), genus *Stagonospora* such as wheat Glume blotch (*Stagonospora nodorum*), genus *Rhynchosporium* such as barley scald (*Rhynchosporium secalis*), genus *Pseudocercosporella* such as wheat eyespot (*Pseudocercosporella herpotrichoides*), genus *Gaeumannomyces* such as wheat take-all (*Gaeumannomyces graminis*), genus *Fusarium* such as wheat *Fusarium* head blight (*Fusarium* spp.), genus *Microdochium* such as wheat snow mold (*Microdochium nivale*), genus *Venturia* such as apple scab (*Venturia inaequalis*), genus *Elsinoe* such as grape anthracnose (*Elsinoe ampelina*), genus *Botrytis* such as cucumber gray mold (*Botrytis cinerea*), genus *Monilinia* such as peach brown rot (*Monilinia fructicola*), genus *Phoma* such as rape stem canker (*Phoma lingam*), genus *Cladosporium* such as tomato leaf mold (*Cladosporium fulvum*), genus *Cercospora* such as sugarbeet brown spot (*Cercospora beticola*), genus *Cercosporidium* such as peanut late leaf spot (*Cercosporidium personatum*), genus *Colletotrichum* such as strawberry anthracnose (*Colletotrichum fragariae*), genus *Sclerotinia* such as cucumber stem rot (*Sclerotinia sclerotiorum*), genus *Alternaria* such as apple necrotic leaf spot (*Alternaria mali*), genus *Verticillium* such as eggplant *verticillium* wilt (*Verticillium dahliae*), genus *Rhizoctonia* such as rice sheath blight (*Rhizoctonia solani*), genus *Puccinia* such as wheat leaf rust (*Puccinia recondita*), genus *Phakopsora* such as soybean rust (*Phakopsora pachyrhizi*), genus *Tilletia* such as wheat bunt (*Tilletia caries*), genus *Ustilago* such as barley loose smut (*Ustilago nuda*), genus *Sclerotium* such as peanut southern blight (*Sclerotium rolfsii*), genus *Phytophthora* such as potato late blight (*Phytophthora infestans*), genus *Pseudoperonospora* such as cucumber downy mildew (*Pseudoperonospora cubensis*), genus *Peronospora* such as Chinese cabbage downy mildew (*Peronospora parasitica*), genus *Plasmopara* such as grape downy mildew (*Plamospara viticola*), genus *Sclerophthora* such as rice downy mildew (*Sclerophthora macrospora*), genus *Pythium* such as cucumber seedling damping-off (*Pythium ultimum*), and genus *Plasmodiophora* such as rapeseed clubroot (*Plasmodiophora brassicae*). Examples of bacteria include genus *Burkholderia* such as bacterial rice seedling blight (*Burkholderia plantarii*), genus *Pseudomonas* such as bacterial cucumber leaf spot (*Pseudomonas syringae* pv. *Lachrymans*), genus *Ralstonia* such as eggplant wilting (*Ralstonia solanacearum*), genus *Xanthomonas* such as Asiatic citrus canker (*Xanthomonas citiri*), and genus *Erwinia* such as Chinese cabbage bacterial soft rot (*Erwinia carotovora*).

Examples of viruses include Tobacco mosaic virus and Cucumber mosaic virus. However, the sterilizing spectra should not be limited thereto in any cases.

The plant disease controlling agent of the present invention can be the compound of the present invention itself, but usually, it is used in the form of formulations such as emulsifiable concentrates, wettable powders, granular wettable powders, flowable formulations, dusts and granules produced by mixing it with solid carriers, liquid carriers, surface active agents and other auxiliary agents for formulation. These formulations usually contain the compound of the present invention in an amount of 0.1 to 90% by weight.

Examples of the solid carriers used in the formulations include fine powders or particles of minerals such as kaolin clay, attapulgite clay, bentonite, montmbrillonite, acid clay, pyrophyllite, talc, diatomaceous earth, and calcite; natural organic substances such as corncob powder, and walnut shell flour; synthetic organic substances such as urea; salts such as calcium carbonate, and ammonium sulfate; and synthetic inorganic substances such as synthetic hydrated silicon oxide. Examples of the liquid carriers include aromatic hydrocarbons such as xylene, alkylbenzene and methylnaphthalene; alcohols such as 2-propanol, ethylene glycol, propylene glycol and cellosolve; ketones such as acetone, cyclohexanone and isophorone; vegetable oils such as soybean oil and cotton seed oil; petroleum aliphatic hydrocarbons; esters; and dimethyl sulfoxide, acetonitrile and water.

Examples of the surfactant include anionic surfactants such as alkyl sulfate, alkyl aryl sulfonate, dialkyl sulfosuccinate, polyoxyethylene alkyl aryl ether phosphate, ligninsulfonate and a naphthalene-sulfonate formaldehyde polycondensate; and nonionic surfactants such as polyoxyethylene alkyl aryl ether, a polyoxyethylene alkyl polyoxypropylene block copolymer and sorbitan fatty acid ester.

Examples of the auxiliary agent for formulation include water-soluble polymers such as polyvinyl alcohol and polyvinyl pyrrolidone; polysaccharides such as gum Arabic, alginic acid and a salt thereof, CMC (carboxymethyl cellulose) and xanthan gum; inorganic substances such as aluminum magnesium silicate, and alumina sol; preservatives; colorants; PAP (acidic isopropyl phosphate); and stabilizers such as BHT.

The plant disease controlling agent of the present invention is used for treating plants to protect the plants from plant diseases, and is also used for treating soil to protect plants growing in the soil from plant diseases.

When the plant disease controlling composition of the present invention is used by subjecting plants to a foliage treatment or used by treating soil, its application amount varies depending upon the kind of crops as plants to be protected, the kind of diseases to be controlled, severity of diseases, form of the formulation, time of application, weather conditions and the like. The total amount of the compound of the present invention is usually within a range of from 1 to 5,000 g, and preferably 5 to 1,000 g per 10,000 m$^2$.

Emulsifiable concentrates, wettable powders and flowable formulations are usually used for treatment by spraying after dilution with water. In this case, the concentration of the compound of the present invention is usually within a range of from 0.0001 to 3% by weight, and preferably from 0.0005 to 1% by weight. Dusts and granules are usually used for a treatment without being diluted.

The plant disease controlling agent of the present invention can be used by a treating method such as seed disinfection. Examples of the method include a method of immersing seeds of plants in the plant disease controlling agent of the present invention in which the concentration of the compound of the present invention is adjusted within a range of from 1 to 1,000 ppm, a method of spraying or smearing the plant disease controlling agent of the present invention in which the concentration of the compound of the present invention is adjusted within a range of from 1 to 1,000 ppm, on seeds of plants, and a method of dust coating of seeds of plants using the plant diseases controlling agent of the present invention.

The plant disease controlling method of the present invention is usually carried out by treating a plant in which onset of diseases is presumed, or soil where the plant is growing, with an effective amount of the plant disease controlling agent of the present invention, and/or treating a plant in which onset of diseases has been confirmed, or the soil where the plants are growing.

The plant disease controlling agent of the present invention can be used as a controlling agent for plant diseases in crop lands such as upland fields, paddy fields, lawn, and orchards, etc. The plant disease controlling agent can control plant diseases in crop lands where the following "crops" or the like are cultivated.

Field crops: corn, rice, wheat, barley, rye, oat, sorghum, cotton, soybean, peanut, buckwheat, beet, rape, sunflower, sugarcane, tobacco, etc.

Vegetables: solanaceae (e.g. eggplant, tomato, green pepper, pepper and potato), Cucurbitaceae (e.g. cucumber, pumpkin, zucchini, watermelon and melon), Cruciferae (e.g. Japanese radish, turnip, horseradish, kohlrabi, Chinese cabbage, cabbage, leaf mustard, broccoli and cauliflower), Compositae (e.g. edible burdock, garland chrysanthemum, globe artichoke and lettuce), Liliacede (e.g., Welsh onion, onion, garlic and asparagus), Umbelliferae (e.g. carrot, parsley, celery and pastinaca), Chenopodiaceae (e.g. spinach and chard), Lamiaceae (e.g. *perilla*, mint and basil), strawberry, sweet potato, Chinese yam, taro, etc.

Flowers and ornament plants.

Ornamental foliage plants.

Fruit trees: pomaceous fruits (e.g. apple, pear, Japanese pear, Chinese quince and quince), stone fruits (e.g. peach, plum, nectarine, Japanese apricot, cherry, apricot and prune), citrus fruits (e.g. satsuma mandarin, orange, lemon, lime and grapefruit), nut trees (e.g. chestnut, walnut, hazel, almond, pistachio, cashew nut and *macadamia* nut), berries (blueberry, cranberry, blackberry and raspberry), grape, Japanese persimmon, olive, loquat, banana, coffee, date palm, coconut palm, etc.

Trees other than fruit trees: tea, mulberry, flowering trees and shrubs, street trees (e.g. Japanese ash, birch, flowering dogwood, blue gum, ginkgo, lilac, maple, oak, poplar, Chinese redbud, Formosa sweet gum, plane tree, zelkova, Japanese arborvitae, fir, Japanese hemlock, needle juniper, pine, Japanese spruce and Japanese yew), etc.

The above-described "crops" include crops having resistance to herbicides such as HPPD inhibitors (e.g. isoxaflutole), ALS inhibitors (e.g. imazethapyr and thifensulfuron-methyl), EPSP synthetase inhibitors, glutamine synthetase inhibitors, bromoxynil, etc. which has been imparted by a classic breeding method or a genetic recombination technology.

Examples of the "crops" having the resistance imparted by the classic breeding method include Clearfield® canola resistant to imidazolinone herbicides (e.g. imazethapyr) and STS soybean resistant to sulfonylurea ALS inhibition type herbicides (e.g. thifensulfuron-methyl). As crops having the resistance imparted by the genetic recombination technology, corn cultivars resistant to glyphosate and glufosinate are exemplified and are already on the market under the trade names of RoundupReady® and LibertyLink®.

The above-described "crops" include crops which have been enabled by the genetic recombination technology to synthesize a selective toxin known in the case of, for example *Bacillus*.

Examples of toxins produced in such genetically modified plants include insecticidal proteins derived from *Bacillus cereus* and *Bacillus popilliae*; insecticidal proteins such as δ-endotoxins (e.g. Cry1Ab, Cry1Ac, Cry1F, Cry1Fa2, Cry2Ab, Cry3A, Cry3Bb1 and Cry9C), VIP 1, VIP 2, VIP 3, VIP 3A, etc., which are derived from *Bacillus thuringiensis*; toxins derived from nematodes; toxins produced by animals, such as scorpion toxin, spider toxin, bee toxin, insect-specific neurotoxins, etc.; filamentous fungi toxins; plant lectins; agglutinin; protease inhibitors such as trypsin inhibitors, serine protease inhibitors, patatin, cystatin, papain inhibitors, etc.; ribosome-inactivating proteins (RIPs) such as ricin, corn-RIP, abrin, rufin, sapolin, briodin, etc.; steroid metabolic enzymes such as 3-hydroxysteroid oxidase, ecdysteroid-UDP-glucosyltransferase, cholesterol oxidase, etc.; ecdysone inhibitors; HMG-COA reductase; ion channel inhibitors such as sodium channel inhibitors, calcium channel inhibitors, etc.; juvenile hormone esterase; diuretic hormone receptors; stilbene synthetase; bibenzyl synthetase; chitinase; and glucanase.

The toxins produced in such genetically engineered crops also include hybrid toxins, partly deficient toxins and modified toxins of insecticidal proteins such as δ-endotoxin proteins (e.g. Cry1Ab, Cry1Ac, Cry1F, Cry1Fa2, Cry2Ab, Cry3A, Cry3Bb1 and Cry9C), VIP 1, VIP 2, VIP 3, VIP 3A, etc. The hybrid toxins are produced by a novel combination of the different domains of such proteins by adopting a genetic recombination technology. As the partly deficient toxin, Cry1Ab deficient in a part of the amino acid sequence is known. In the modified toxins, one or more amino acids of a natural toxin have been replaced.

Examples of such toxins and genetically modified plants capable of synthesizing such toxins are described in EP-A-0 374 753, WO 93/07278, WO 95/34656, EP-A-0 427 529, EP-A-451 878, WO 03/052073, etc.

The toxins contained in such genetically engineered plants impart resistance to insect pests of Coleoptera, insect pests of Diptera and insect pests of *Lepidoptera* to the plants.

Genetically engineered plants containing one or more insecticidal insect-resistant genes and capable of producing one or more toxins have already been known, and some of them are on the market. Examples of such genetically modified plants include YieldGard® (a corn cultivar capable of producing Cry1Ab toxin), YieldGard Rootworm® (a corn cultivar capable of producing Cry3Bb1 toxin), YieldGard Plus® (a corn cultivar capable of producing Cry1Ab and Cry3Bb1 toxins), Herculex I® (a corn cultivar capable of producing phosphinotrysin N-acetyltransferase (PAT) for imparting resistance to Cry1Fa2 toxin and Glyfosinate), NuCOTN33B (a cotton cultivar capable of producing Cry1Ac toxin), Bollgard I® (a cotton cultivar capable of producing Cry1Ac toxin), Bollgard II® (a cotton cultivar capable of producing Cry1Ac and Cry2Ab toxins), VIP-COT® (a cotton cultivar capable of producing VIP toxin), NewLeaf® (a potato cultivar capable of producing Cry3A toxin), NatureGard®, Agrisure®, GT Advantage (GA$^{21}$ glyphosate resistant properties), Agrisure® CB Advantage (Btll corn borer (CB) properties), and Protecta®.

The above-mentioned "crops" also include crops having an ability to produce an anti-pathogenic substance having a selective action which has been imparted by a genetic recombination technology.

As examples of the anti-pathogenic substance, PR proteins and the like are known (PRPs, EP-A-0 392 225). Such anti-pathogenic substances and genetically engineered plants capable of producing them are described in EP-A-0 392 225, WO 95/33818, EP-A-0 353 191, and the like.

Examples of such anti-pathogenic substances produced by the genetically modified plants include ion channel inhibitors such as sodium channel inhibitors, calcium channel inhibitors (for example, KP1, KP4, and KP6 toxins produced by viruses are known), etc.; stilbene synthase; bibenzyl synthase; chitinase; glucanase; PR proteins; and anti-pathogenic substances produced by microorganisms, such as peptide antibiotics, antibiotics having a heterocyclic ring, protein factors concerned in resistance to plant diseases (which are called plant-disease-resistant genes and are described in WO 03/000906), etc.

It is also possible to use the plant disease controlling agent of the present invention after mixing with other fungicides, insecticides, acaricides, nematocides, herbicides, plant growth regulators, fertilizers or soil conditioners, or to use the agent without mixing them. Examples of the active ingredients of the plant disease controlling agent include chlorothalonil, fluazinam, dichlofluanid, fosetyl-Al, cyclic imide derivatives (e.g., captan, captafol, folpet, etc.), dithiocarbamate derivatives (e.g., maneb, mancozeb, thiuram, ziram, zineb, propineb, etc.), inorganic or organic copper derivatives (e.g., basic copper sulfate, basic copper chloride, copper hydroxide, oxine-copper, etc.), acylalanine derivatives (e.g., metalaxyl, furalaxyl, ofurace, cyprofuram, benalaxyl, oxadixyl, etc.), strobilurine like compound (e.g., kresoxim-methyl, azoxystrobin, trifloxystrobin, picoxystrobin, pyraclostrobin, fluoxastrobin, metominostrobin, orysastrobin, enestrobin, dimoxystrobin, etc.), anilinopyrimidine derivatives (e.g., cyprodinil, pyrimethanil, mepanipyrim, etc.), phenyl pyrrole derivatives (e.g., fenpiclonil, fludioxonil, etc.), imide derivatives (e.g., procymidone, iprodione, vinclozolin, etc.), benzimidazole derivatives (e.g., carbendazim, benomyl, thiabendazole, thiophanate methyl, etc.), amine derivatives (e.g., fenpropimorph, tridemorph, fenpropidin, spiroxamine, etc.), azole derivatives (e.g., propiconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, flutriafol, ipconazole, pefurazoate, prothioconazole, etc.), triforine, pyrifenox, fenarimol, propamocarb, cymoxanil, dimethomorph, flumorph, famoxadone, fenamidone, pyribencarb, iprovalicarb, benthiavalicarb, mandipropamid, cyazofamid, amisulbrom, zoxamide, ethaboxam, boscalid, penthiopyrad, fluopyram, bixafen, carboxin, oxycarboxin, thifluzamide, flutolanil, mepronil, furametpyr, pencycuron, hymexazol, etridiazole, ferimzone, silthiofam, blasticidin S, kasugamycin, streptomycin, pyrazophos, iprobenfos, edifenphos, isoprothiolane, fthalide, pyroquilon, tricyclazole, carpropamid, diclocymet, fenoxanil, probenazole, tiadinil, isotianil, iminoctadine, guazatine, tolnifanide, tolclophos-methyl, fenhexamid, polyoxin B, quinoxyfen, proquinazid, metrafenone, cyflufenamid, diethofencarb, fluopicolide and acibenzolar-S-methyl.

EXAMPLES

Hereinafter, the present invention will be described in more detail by way of Production Examples, Formulation Examples and Test Example which the present invention is not limited to.

First, Production Examples of the compound of the present invention will be described.

Production Example 1

To 5 ml of THF were added 0.23 g of 2,5-difluoro-4-(2-propynyloxy)benzoyl chloride, 0.28 g of 2-hydroxy-1,2-dimethylpropylamine hydrochloride and 0.4 ml of triethylamine, and the mixture was stirred at room temperature for 12 hours. The reaction mixture was subjected to silica gel column chromatography, and 0.23 g of N-(2-hydroxy-1,2-dimethylpropyl)-2,5-difluoro-4-(2-propynyloxy)benzamide (hereinafter, referred to as a compound 1 of the present invention) was obtained. The compound 1 of the present invention

[Chemical formula 16]

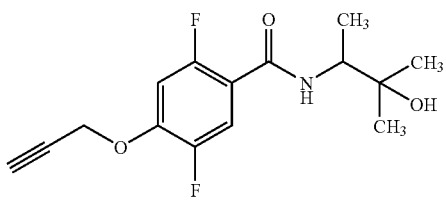

$^1$H-NMR (CDCl$_3$) δ: 1.24-1.29 (9H, m), 2.15 (1H, s), 2.61 (1H, t, J=2.4 Hz), 4.13-4.19 (1H, m), 4.81 (2H, d, J=2.4 Hz), 6.88 (1H, dd, J=12.7, 6.4 Hz), 6.92-6.97 (1H, m), 7.83 (1H, dd, J=11.6, 7.2 Hz).

Production Example 2

N-{1-(hydroxymethyl)cyclohexyl}methyl-2,5-difluoro-4-(2-propynyloxy)benzamide (hereinafter, referred to as a compound 2 of the present invention) was obtained according to a process described in Production Example 1 except that 1-{1-(hydroxymethyl)cyclohexyl}methylamine was used in place of 2-hydroxy-1,2-dimethylpropylamine hydrochloride. The compound 2 of the present invention

[Chemical formula 17]

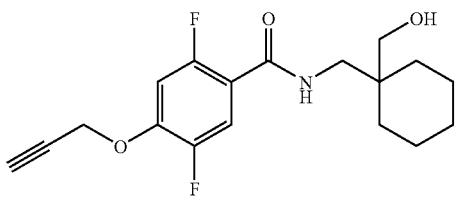

$^1$H-NMR (CDCl$_3$) δ: 1.24-1.49 (10H, m), 2.61 (1H, t, J=2.4 Hz), 3.36 (2H, d, J=7.0 Hz), 3.42 (2H, dd, J=6.6, 1.3 Hz), 3.59 (1H, t, J=7.0 Hz), 4.81 (2H, d, J=2.4 Hz), 6.88 (1H, dd, J=12.8, 6.5 Hz), 7.00-7.05 (1H, m), 7.84 (1H, dd, J=11.6, 7.2 Hz).

Production Example 3

N-(1-cyclohexenyl)methyl-2,5-difluoro-4-(2-propynyloxy)benzamide (hereinafter, referred to as a compound 3 of the present invention) was obtained according to a process described in Production Example 1 except that 1-cyclohexenylmethylamine hydrochloride was used in place of 2-hydroxy-1,2-dimethylpropylamine hydrochloride. The compound 3 of the present invention

[Chemical formula 18]

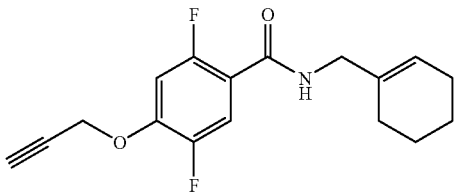

$^1$H-NMR (CDCl$_3$) δ: 1.55-1.68 (4H, m), 1.96-2.05 (4H, m), 2.61 (1H, t, J=2.4 Hz), 3.97 (2H, d, J=5.6 Hz), 4.81 (2H, d, J=2.4 Hz), 5.63-5.65 (1H, m), 6.64-6.69 (1H, m), 6.87 (1H, dd, J=12.7, 6.4 Hz), 7.86 (1H, dd, J=11.6, 7.2 Hz).

Production Example 4

N-(2-oxocyclohexyl)-2,5-difluoro-4-(2-propynyloxy)benzamide (hereinafter, referred to as a compound 4 of the present invention) was obtained according to a process described in Production Example 1 except that 2-aminocyclohexanone hydrobromide was used in place of 2-hydroxy-1,2-dimethylpropylamine hydrochloride. The compound 4 of the present invention

[Chemical formula 19]

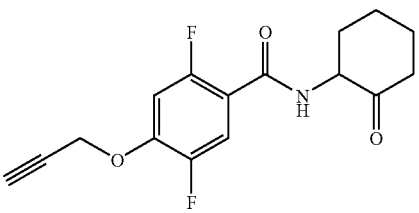

$^1$H-NMR (CDCl$_3$) δ: 1.46 (1H, ddd, J=25.1, 12.6, 4.3 Hz), 1.70 (1H, tdd, J=17.4, 8.6, 4.5 Hz), 1.81-1.97 (2H, m), 2.15-2.22 (1H, m), 2.45 (1H, tdd, J=13.5, 6.1, 1.1 Hz), 2.56-2.62 (2H, m), 2.76-2.84 (1H, m), 4.64-4.70 (1H, m), 4.81 (2H, d, J=2.4 Hz), 6.90 (1H, dd, J=12.6, 6.5 Hz), 7.68-7.72 (1H, m), 7.81 (1H, dd, J=11.6, 7.2 Hz).

The following Reference Production Examples show production of intermediates for producing the compound of the present invention.

Reference Production Example 1

To 50 ml of water were added 10 g of 2,3,4,5-tetrafluorobenzoic acid and 4.5 g of sodium hydroxide, and the mixture was heated to reflux for 4 hours. The reaction mixture was made acidic by addition of hydrochloric acid, extracted with ethyl acetate, and then washed sequentially with water and an aqueous saturated sodium chloride solution. The organic layer was dried over magnesium sulfate, and then concentrated under reduced pressure, and the residue was obtained.

The residue, 14 g of propargyl bromide and 18 g of potassium carbonate were added to 100 ml of DMF, and the mixture was stirred at room temperature for 1 day. The reaction mixture was added to water, made acidic by addition of diluted hydrochloric acid, and then extracted with ethyl acetate. The organic layer was washed sequentially with water and aqueous saturated sodium chloride solution, dried, and then concentrated under reduced pressure. The residue was subjected to silica gel column chromatography, and 6.5 g of 2-propynyl 4-(2-propynyloxy)-2,3,5-trifluorobenzoate was obtained.

2-Propynyl 4-(2-propynyloxy)-2,3,5-trifluorobenzoate

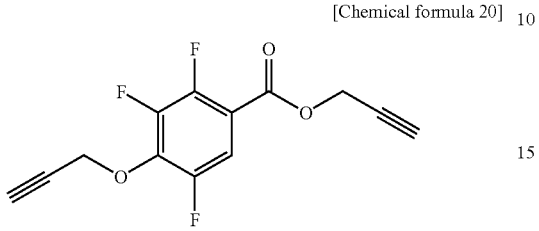

[Chemical formula 20]

$^1$H-NMR (CDCl$_3$) δ: 2.55 (1H, t, J=2.4 Hz), 2.57 (1H, t, J=2.4 Hz), 4.94 (2H, d, J=2.4 Hz), 4.96 (2H, d, J=2.4 Hz), 7.55 (1H, ddd, J=11.1, 6.1, 2.3 Hz).

To a mixture of 10 ml of THF and 10 ml of water were added 6.5 g of 2-propynyl 4-(2-propynyloxy)-2,3,5-trifluorobenzoate obtained above and 2.0 g of lithium hydroxide monohydrate, and the mixture was stirred at room temperature for 2 hours and at 50° C. for 2 hours. The reaction mixture was concentrated under reduced pressure until the total volume became about a half. Then, the concentrated reaction mixture was made acidic by addition of hydrochloric acid, and the resulting solid was collected by filtration. The solid was dried and then washed with hexane, and 4.0 g of 4-(2-propynyloxy)-2,3,5-trifluorobenzoic acid was obtained.

4-(2-Propynyloxy)-2,3,5-trifluorobenzoic acid

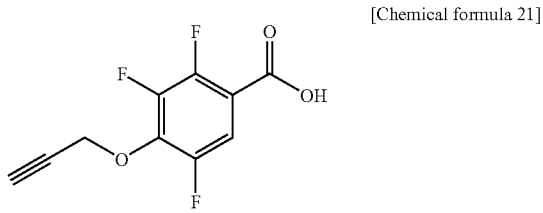

[Chemical formula 21]

$^1$H-NMR (DMSO-d$_6$) δ: 3.72-3.74 (1H, m), 5.04 (2H, d, J=2.2 Hz), 7.60 (1H, ddd, J=11.2, 6.5, 2.3 Hz)

Reference Production Example 2

To 5 ml of water were added 1.0 g of 2,4,5-trifluorobenzoic acid and 0.9 g of sodium hydroxide, and the mixture was stirred at 160° C. for 10 minutes using a microwave reaction apparatus. The same procedure was repeated five times. As a result, a total of 5.0 g of 2,4,5-trifluorobenzoic acid was used. All of the obtained reaction mixtures were mixed, made acidic by addition of hydrochloric acid, and then extracted with ethyl acetate. The organic layer was concentrated under reduced pressure, and the residue was obtained.

To 50 ml of DMF were added the residue obtained by the above operation, 9.0 g of propargyl bromide and 10 g of potassium carbonate, and the mixture was stirred at room temperature for 2 days. The reaction mixture was added to water, and then extracted with ethyl acetate. The organic layer was dried over magnesium sulfate, and concentrated under reduced pressure. The residue was subjected to silica gel column chromatography, and 7.3 g of 2-propynyl 2,5-difluoro-4-(2-propynyloxy)benzoate was obtained.

2-Propynyl 2,5-difluoro-4-(2-propynyloxy)benzoate

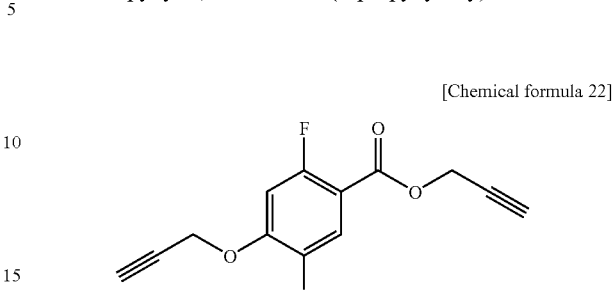

[Chemical formula 22]

$^1$H-NMR (CDCl$_3$) δ: 2.53 (1H, t, J=2.4 Hz), 2.63 (1H, t, J=2.4 Hz), 4.82 (2H, d, J=2.2 Hz), 4.91 (2H, d, J=2.4 Hz), 6.90 (1H, dd, J=11.6, 6.7 Hz), 7.71 (1H, dd, J=11.1, 6.7 Hz).

To a mixture of 20 ml of methanol and 20 ml of a 15% aqueous sodium hydroxide solution was added 7.3 g of 2-propynyl 2,5-difluoro-4-(2-propynyloxy)benzoate, and the mixture was stirred at 50° C. for 2 hours. The reaction mixture was added to hydrochloric acid, and a produced solid was collected by filtration. The solid was dried and then washed with hexane, and 3.8 g of 2,5-difluoro-4-(2-propynyloxy)benzoic acid was obtained.

2,5-Difluoro-4-(2-propynyloxy)benzoic acid

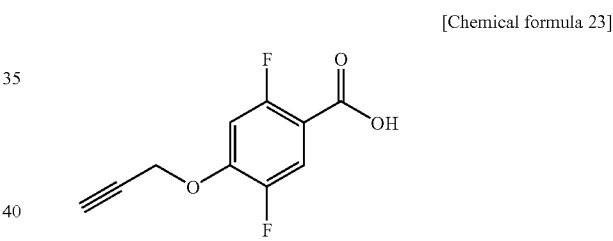

[Chemical formula 23]

$^1$H-NMR (CDCl$_3$) δ: 2.64 (1H, t, J=2.4 Hz), 4.83 (2H, d, J=2.4 Hz), 6.92 (1H, dd, J=11.5, 6.6 Hz), 7.75 (1H, dd, J=11.1, 6.7 Hz).

To 20 ml of toluene were added 1.4 g of 2,5-difluoro-4-(2-propynyloxy)benzoic acid, 0.8 ml of thionyl chloride and 10 mg of DMF, and the mixture was heated to reflux for 2 hours. Then, the reaction mixture was concentrated under reduced pressure, and 1.5 g of 2,5-difluoro-4-(2-propynyloxy)benzoyl chloride was obtained.

2,5-Difluoro-4-(2-propynyloxy)benzoyl chloride

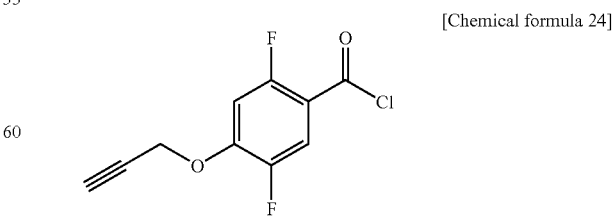

[Chemical formula 24]

$^1$H-NMR (CDCl$_3$) δ: 2.66 (1H, t, J=2.4 Hz), 4.86 (2H, d, J=2.4 Hz), 6.94 (1H, dd, J=11.7, 6.6 Hz), 7.88 (1H, dd, J=11.1, 6.7 Hz).

Reference Production Example 3

To a mixture of 150 ml of DMF, 12.7 g of 2-propynyl 2-chloro-4,5-difluorobenzoate and 3.4 g of propargyl alcohol was added 2.4 g of 60% sodium hydride (oily) under ice-cooling. The reaction mixture was stirred at room temperature overnight. Hydrochloric acid was added to the reaction mixture, followed by extraction with ethyl acetate. The resulting organic layer was washed sequentially with water and an aqueous saturated sodium chloride solution, dried over magnesium sulfate, and then concentrated under reduced pressure. The resulting residue was subjected to silica gel column chromatography, and 19 g of 2-propynyl 2-chloro-5-fluoro-4-(2-propynyloxy)benzoate was obtained.

To a mixture of 30 ml of methanol and 30 ml of a 15% aqueous sodium hydroxide solution was added 19 g of 2-propynyl 2-chloro-5-fluoro-4-(2-propynyloxy)benzoate obtained above, and then stirred at 50° C. for 2 hours. The reaction mixture was made acidic by addition of hydrochloric acid. Then, a produced solid was collected by filtration. The solid was washed with a MTBE-hexane mixed solvent, and 10 g of 2-chloro-5-fluoro-4-(2-propynyloxy)benzoic acid was obtained.

2-Chloro-5-fluoro-4-(2-propynyloxy)benzoic acid

[Chemical formula 25]

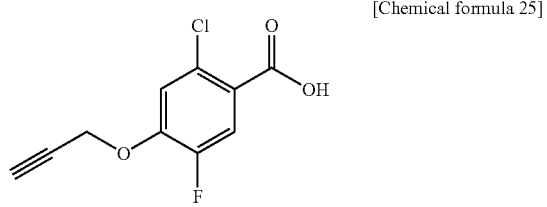

$^1$H-NMR (DMSO-$d_6$) δ: 3.69 (1H, t, J=2.3 Hz), 5.01 (2H, d, J=2.3 Hz), 7.37 (1H, d, J=7.6 Hz), 7.65 (1H, d, J=11.7 Hz).

Then, Formulation Examples are shown. The term "part(s)" represents part(s) by weight.

Formulation Example 1

50 parts of each of the compounds 1 to 4 of the present invention, 3 parts of calcium ligninsulfonate, 2 parts of magnesium laurylsulfate and 45 parts of synthetic hydrated silica are pulverized and mixed well to give a wettable powder of each compound.

Formulation Example 2

20 parts of each of the compounds 1 to 4 of the present invention and 1.5 parts of sorbitan trioleate are mixed with 28.5 parts of an aqueous solution containing 2 parts of polyvinyl alcohol, and wet-pulverized finely. To the obtained mixture, 40 parts of an aqueous solution containing 0.05 part of xanthan gum and 0.1 part of aluminium magnesium silicate is added and further 10 parts of propylene glycol is added. The mixture was stirred and mixed to give a flowable of each compound.

Formulation Example 3

2 parts of each of the compounds 1 to 4 of the present invention, 88 parts of kaolin clay and 10 parts of talc are pulverized and mixed well to give a dust of each compound.

Formulation Example 4

5 parts of each of the compounds 1 to 4 of the present invention, 14 parts of polyoxyethylenestyryl phenyl ether, 6 parts of calcium dodecylbenzenesulfonate and 75 parts of xylene are mixed well to give an emulsifiable concentrate of each compound.

Formulation Example 5

2 parts of each of the compounds 1 to 4 of the present invention, 1 part of synthetic hydrated silica, 2 parts of calcium ligninsulfonate, 30 parts of bentonite and 65 parts of kaolin clay are pulverized and mixed well, and water is added thereto and kneaded well, granulated and dried to give granules of each compound.

Formulation Example 6

10 parts of each of the compounds 1 to 4 of the present invention, 35 parts of white carbon containing 50 parts of ammonium polyoxyethylenealkyl ether sulfate, and 55 parts of water are mixed and wet pulverized finely to give a formulation of each compound.

The following Test Examples show that the compounds of the present invention are useful for controlling a plant disease.

The controlling effect was evaluated by visually observing the area or lesion spots on each of test plants at the time of investigation and comparing the area of lesion spots on a plant treated with the compound of the present invention with that on an untreated plant.

Test Example

Test of Preventive Effect on Tomato Late Blight (*Phytophthora infestans*)

Each of plastic pots was filled with sandy loam and sown with tomato (cultivar; Patio), followed by growing in a greenhouse for 20 days. Each of the present compounds 1 to 4 was formulated into a flowable formulation according to Formulation Example 6. The flowable formulation was diluted to a predetermined concentration (200 ppm) with water, and foliage application was carried out so that the dilution adhered sufficiently to the surfaces of leaves of the grown tomato young seedling. After the plant was air-dried so that the diluted solution on leaves was dried, a water suspension of zoosporangia of *Phytophthora infestans* was sprayed. After the inoculation, the plant was held under high humidity conditions at 23° C., for 1 day and held in a greenhouse for 4 days, and then the area of lesion spots was investigated. As a result, it was found that the area of lesion spots on the plant treated with any one of the present compounds 1 to 4 was 30% or less of that an untreated plant.

INDUSTRIAL APPLICABILITY

As described above, according to the present invention, an amide compound having excellent plant disease controlling activity which is useful as an active ingredient of a plant disease controlling agent can be provided.

The invention claimed is:
1. An amide compound represented by the formula (1):

[Chemical formula 1]

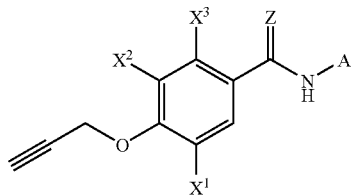

(1)

wherein
X¹ represents a fluorine atom or a methoxy group,
X² represents a hydrogen atom, a halogen atom, a $C_1$-$C_4$ alkyl group, a $C_2$-$C_4$ alkenyl group, a $C_2$-$C_4$ alkynyl group, a $C_1$-$C_4$ haloalkyl group, a $C_1$-$C_4$ alkoxy group, a $C_1$-$C_4$ alkylthio group, a hydroxy $C_1$-$C_4$ alkyl group, a nitro group, a cyano group, a formyl group, an $NR^1R^2$ group, a $CO_2R^3$ group, a $CONR^4R^5$ group, or a phenyl group optionally substituted with at least one group selected from the group consisting of a methyl group, a halogen atom, a cyano group and a nitro group,
X³ represents a halogen atom, a $C_1$-$C_4$ alkyl group, a $C_2$-$C_4$ alkenyl group, a $C_2$-$C_4$ alkynyl group, a $C_1$-$C_4$ haloalkyl group, a $C_1$-$C_4$ alkoxy group, a $C_1$-$C_4$ alkylthio group, a nitro group, a cyano group, a formyl group, an $NR^6R^7$ group, a $CO_2R^8$ group, a $CONR^9R^{10}$ group, or a phenyl group optionally substituted with at least one group selected from the group consisting of a methyl group, a halogen atom, a cyano group and a nitro group,
Z represents an oxygen atom or a sulfur atom,
A represents a group represented by $A^1$-$CR^{11}R^{12}R^{13}$, $A^2$-$Cy^1$ or $A^3$-$Cy^2$,
$A^1$ represents a $CH_2$ group, a $CH(CH_3)$ group, a $C(CH_3)_2$ group or a $CH(CH_2CH_3)$ group,
$A^2$ represents a single bond, a $CH_2$ group, a $CH(CH_3)$ group, a $C(CH_3)_2$ group or a $CH(CH_2CH_3)$ group,
$A^3$ represents a methylene group substituted with at least one group selected from the group consisting of a $C_1$-$C_3$ haloalkyl group, a $C_2$-$C_4$ alkenyl group, a $C_2$-$C_4$ alkynyl group, a cyano group, a phenyl group and a $C_2$-$C_5$ alkoxycarbonyl group,
$Cy^1$ represents a $C_3$-$C_6$ cycloalkyl group substituted with at least one group selected from the following group [a-1], a $C_3$-$C_6$ cycloalkenyl group optionally substituted with at least one group selected from the following group [a-1], a $C_3$-$C_6$ cycloalkyl group which is optionally substituted with at least one group selected from the following group [a-1] and in which one of methylenes forming the ring is replaced with a carbonyl group, or a $C_3$-$C_6$ hydroxyiminocycloalkyl group optionally substituted with at least one group selected from the following group [a-1],
$Cy^2$ represents a $C_3$-$C_6$ cycloalkyl group optionally substituted with at least one group selected from the following group [a-2], a $C_3$-$C_6$ cycloalkenyl group optionally substituted with at least one group selected from the following group [a-2], a $C_3$-$C_6$ cycloalkyl group which is optionally substituted with at least one group selected from the following group [a-2] and in which one of methylenes forming the ring is replaced with a carbonyl group, or a $C_3$-$C_6$ hydroxyiminocycloalkyl group optionally substituted with at least one group selected from the following group [a-2],
$R^1$ and $R^2$ independently represent a hydrogen atom, a $C_1$-$C_4$ alkyl group, a $C_3$-$C_4$ alkenyl group, a $C_3$-$C_4$ alkynyl group, a $C_2$-$C_4$ haloalkyl group, a $C_2$-$C_5$ alkylcarbonyl group, a $C_2$-$C_5$ alkoxycarbonyl group or a $C_1$-$C_4$ alkylsulfonyl group,
$R^3$ represents a $C_1$-$C_4$ alkyl group, a $C_3$-$C_4$ alkenyl group or a $C_3$-$C_4$ alkynyl group,
$R^4$ represents a hydrogen atom, a $C_1$-$C_4$ alkyl group, a $C_3$-$C_4$ alkenyl group, a $C_3$-$C_4$ alkynyl group, a $C_2$-$C_4$ haloalkyl group, a $C_2$-$C_5$ alkylcarbonyl group, a $C_2$-$C_5$ alkoxycarbonyl group or a $C_1$-$C_4$ alkylsulfonyl group,
$R^5$ represents a hydrogen atom, a $C_1$-$C_4$ alkyl group, a $C_3$-$C_4$ alkenyl group, a $C_3$-$C_4$ alkynyl group, or a $C_2$-$C_4$ haloalkyl group,
$R^6$ and $R^7$ independently represent a hydrogen atom, a $C_1$-$C_4$ alkyl group, a $C_3$-$C_4$ alkenyl group, a $C_3$-$C_4$ alkynyl group, a $C_2$-$C_4$ haloalkyl group, a $C_2$-$C_5$ alkylcarbonyl group, a $C_2$-$C_5$ alkoxycarbonyl group or a $C_1$-$C_4$ alkylsulfonyl group,
$R^8$ represents a $C_1$-$C_4$ alkyl group, a $C_3$-$C_4$ alkenyl group or a $C_3$-$C_4$ alkynyl group,
$R^9$ represents a hydrogen atom, a $C_1$-$C_4$ alkyl group, a $C_3$-$C_4$ alkenyl group, a $C_3$-$C_4$ alkynyl group, a $C_2$-$C_4$ haloalkyl group, a $C_2$-$C_5$ alkylcarbonyl group, a $C_2$-$C_5$ alkoxycarbonyl group or a $C_1$-$C_4$ alkylsulfonyl group,
$R^{10}$ represents a hydrogen atom, a $C_1$-$C_4$ alkyl group, a $C_3$-$C_4$ alkenyl group, a $C_3$-$C_4$ alkynyl group, or a $C_2$-$C_4$ haloalkyl group,
$R^{11}$ and $R^{12}$ independently represent a $C_1$-$C_4$ alkyl group,
$R^{13}$ represents a halogen atom, a hydroxyl group, a $C_1$-$C_6$ alkyl group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a hydroxy $C_1$-$C_6$ alkyl group, a $C_2$-$C_4$ alkylcarbonyloxy group, a $(C_1$-$C_3$ alkylamino)$C_1$-$C_6$ alkyl group, a (di($C_1$-$C_3$)alkyl)amino)$C_1$-$C_6$ alkyl group, a mercapto group, a carbamoyl group, a formyl group, a $C_2$-$C_6$ cyanoalkyl group, a $C_1$-$C_3$ alkylsulfonyl group, a phenoxy group or an $NR^{14}R^{15}$ group [wherein $R^{14}$ and $R^{15}$ independently represent a hydrogen atom, a $C_1$-$C_4$ alkyl group, a $C_2$-$C_5$ alkylcarbonyl group, a $C_2$-$C_5$ alkoxycarbonyl group, or a $C_1$-$C_4$ alkylsulfonyl group];
the group [a-1] consists of:
a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a $C_1$-$C_3$ alkylidene group which forms a double bond with the same carbon atom forming a ring, a hydroxy $C_1$-$C_6$ alkyl group, a $C_2$-$C_4$ alkylcarbonyloxy group, a $(C_1$-$C_3$ alkylamino)$C_1$-$C_6$ alkyl group, a (di($C_1$-$C_3$ alkyl)amino)$C_1$-$C_6$ alkyl group, a mercapto group, a carbamoyl group, a formyl group, a $C_2$-$C_6$ cyanoalkyl group, a $C_1$-$C_3$ alkylsulfonyl group, a phenoxy group, and an $NR^{16}R^{17}$ group [wherein $R^{16}$ and $R^{17}$ independently represent a hydrogen atom, a $C_1$-$C_4$ alkyl group, a $C_2$-$C_5$ alkylcarbonyl group, a $C_2$-$C_5$ alkoxycarbonyl group or a $C_1$-$C_4$ alkylsulfonyl group]; and
the group [a-2] consists of:
a halogen atom, a $C_1$-$C_4$ alkyl group, a $C_2$-$C_4$ alkenyl group, a $C_2$-$C_4$ alkynyl group, a hydroxyl group, a cyano group, a carboxyl group, a $C_2$-$C_5$ alkoxycarbonyl group, a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a $C_1$-$C_3$ alkylidene group which forms a double bond with the same carbon atom forming a ring, a hydroxy $C_1$-$C_6$ alkyl group, a $C_2$-$C_4$ alkylcarbonyloxy group, a $(C_1-C_3$ alkylamino)$C_1-C_6$ alkyl group, a (di$(C_1-C_3$ alkyl)amino)$C_1-C_6$ alkyl group, a mercapto group, a carbamoyl group, a formyl group, a $C_2-C_6$ cyanoalkyl group, a $C_1-C_3$ alkylsulfonyl group, a phenoxy group, and an $NR^{18}R^{19}$ group [wherein $R^{18}$ and $R^{19}$ independently represent a hydrogen atom, a $C_1-C_4$ alkyl group, a $C_2-C_5$ alkylcarbonyl group, a $C_2-C_5$ alkoxycarbonyl group or a $C_1-C_4$ alkylsulfonyl group].

2. The amide compound according to claim 1, wherein $X^3$ is a halogen atom.

3. The amide compound according to claim 1, wherein $X^3$ is a fluorine atom.

4. The amide compound according to claim 1, wherein $X^2$ is a hydrogen atom, a fluorine atom or a methoxy group, and $X^3$ is a fluorine atom.

5. The amide compound according to claim 1, wherein $X^1$ is a fluorine atom.

6. The amide compound according to claim 1, wherein $X^1$ is a methoxy group.

7. The amide compound according to claim 1, wherein A is $A^2$-$Cy^1$, $A^2$ is a single bond, a $CH_2$ group or a $CH(CH_3)$ group, and $Cy^1$ is a cyclohexyl group substituted with a group selected from the group consisting of a $C_1-C_6$ alkoxy group, a $C_1-C_6$ haloalkyl group, a hydroxy $C_1-C_6$ alkyl group and a $C_1-C_3$ alkylcarbonyloxy group.

8. The amide compound according to claim 1, wherein
A is a group represented by $A^1$-$CR^{11}R^{12}R^{13}$, $A^2$-$Cy^1$ or $A^3$-$Cy^2$,
$A^1$ is a $CH_2$ group, a $CH(CH_3)$ group, a $C(CH_3)_2$ group or a $CH(CH_2CH_3)$ group,
$A^2$ is a single bond, a $CH_2$ group, a $CH(CH_3)$ group, a $C(CH_3)_2$ group or a $CH(CH_2CH_3)$ group,
$A^3$ is a methylene group substituted with at least one group selected from the group consisting of a $C_1-C_3$ haloalkyl group, a $C_2-C_4$ alkenyl group, a $C_2-C_4$ alkynyl group, a cyano group and a phenyl group,
$Cy^1$ is a $C_3-C_6$ cycloalkyl group substituted with at least one group selected from the following group [b-1], a $C_3-C_6$ cycloalkenyl group optionally substituted with at least one group selected from the following group [b-1], a $C_3-C_6$ cycloalkyl group which is optionally substituted with at least one group selected from the following group [b-1] and in which one of methylenes forming the ring is replaced with a carbonyl group, or a $C_3-C_6$ hydroxyiminocycloalkyl group optionally substituted with at least one group selected from the following group [b-1],
$Cy^2$ is a $C_3-C_6$ cycloalkyl group optionally substituted with at least one group selected from the following group [b-2], a $C_3-C_6$ cycloalkenyl group optionally substituted with at least one group selected from the following group [b-2], a $C_3-C_6$ cycloalkyl group which is optionally substituted with at least one group selected from the following group [b-2] and in which one of methylenes forming the ring is replaced with a carbonyl group, or a $C_3-C_6$ hydroxyiminocycloalkyl group optionally substituted with at least one group selected from the following group [b-2],
$R^{13}$ is a halogen atom, a hydroxyl group, a $C_1-C_6$ alkoxy group, a $C_3-C_6$ alkenyloxy group, a $C_1-C_6$ haloalkyl group, a $C_1-C_6$ haloalkoxy group, a phenyl group, a benzyl group, a $C_1-C_3$ alkylthio group, a hydroxy $C_1-C_6$ alkyl group, a $C_2-C_4$ alkylcarbonyloxy group, a (di($C_1$-$C_3$ alkyl)amino)$C_1-C_6$ alkyl group, a carbamoyl group, a formyl group, a $C_2-C_6$ cyanoalkyl group, a $C_1-C_3$ alkylsulfonyl group or a phenoxy group;
the group [b-1] consists of:
a $C_1-C_6$ alkoxy group, a $C_3-C_6$ alkenyloxy group, a $C_1-C_6$ haloalkyl group, a $C_1-C_6$ haloalkoxy group, a phenyl group, a benzyl group, a $C_1-C_3$ alkylthio group, a $C_1-C_3$ alkylidene group which forms a double bond with the same carbon atom forming a ring, a hydroxy $C_1-C_6$ alkyl group, a $C_2-C_4$ alkylcarbonyloxy group, a (di($C_1-C_3$ alkyl)amino)$C_1-C_6$ alkyl group, a carbamoyl group, a formyl group, a $C_2-C_6$ cyanoalkyl group, a $C_1-C_3$ alkylsulfonyl group and a phenoxy group; and
the group [b-2] consists of:
a halogen atom, a $C_1-C_4$ alkyl group, a $C_2-C_4$ alkenyl group, a $C_2-C_4$ alkynyl group, a hydroxyl group, a cyano group, a $C_1-C_6$ alkoxy group, a $C_3-C_6$ alkenyloxy group, a $C_1-C_6$ haloalkyl group, a $C_1-C_6$ haloalkoxy group, a phenyl group, a benzyl group, a $C_1-C_3$ alkylthio group, a $C_1-C_3$ alkylidene group which forms a double bond with the same carbon atom forming a ring, a hydroxy $C_1-C_6$ alkyl group, a $C_2-C_4$ alkylcarbonyloxy group, a (di($C_1-C_3$ alkyl)amino)$C_1-C_6$ alkyl group, a carbamoyl group, a formyl group, a $C_2-C_6$ cyanoalkyl group, a $C_1-C_3$ alkylsulfonyl group and a phenoxy group.

9. A plant disease controlling agent which comprises the amide compound according to claim 1 as an active ingredient and an auxiliary agent for formulation.

10. A method of controlling a plant disease which comprises treating a plant or soil with an effective amount of the amide compound according to claim 1.

* * * * *